United States Patent
Zheng et al.

(10) Patent No.: US 11,943,863 B2
(45) Date of Patent: Mar. 26, 2024

(54) ELECTRONICS-TO-TEXTILE INTERCONNECTION METHOD AND SYSTEM

(71) Applicant: MYANT INC., Toronto (CA)

(72) Inventors: Michelle Zheng, Toronto (CA); Adrian Philip Straka, Toronto (CA); Calvin Fook-Lam Kwok, Toronto (CA); Christopher Robin Leiphart, Toronto (CA); Yeh-Yun Tiau, Toronto (CA)

(*) Notice: Subject to any disclaimer, the term of this patent is extended or adjusted under 35 U.S.C. 154(b) by 0 days.

(21) Appl. No.: 17/620,507

(22) PCT Filed: Jun. 25, 2020

(86) PCT No.: PCT/CA2020/050882
§ 371 (c)(1),
(2) Date: Dec. 17, 2021

(87) PCT Pub. No.: WO2020/257933
PCT Pub. Date: Dec. 30, 2020

(65) Prior Publication Data
US 2022/0346227 A1    Oct. 27, 2022

Related U.S. Application Data

(60) Provisional application No. 62/868,560, filed on Jun. 28, 2019.

(51) Int. Cl.
*H05K 1/03* (2006.01)
*A61B 5/00* (2006.01)
*H05K 3/36* (2006.01)

(52) U.S. Cl.
CPC ........... *H05K 1/038* (2013.01); *A61B 5/6804* (2013.01); *H05K 3/361* (2013.01); *H05K 2201/10393* (2013.01)

(58) Field of Classification Search
CPC ....... H05K 1/038; H05K 3/361; A61B 5/6804
(Continued)

(56) References Cited

U.S. PATENT DOCUMENTS 9,028,404 B2    5/2015   Deremer et al.
2009/0215283 A1  8/2009  Du
(Continued)

FOREIGN PATENT DOCUMENTS

DE    102016117762 A1    3/2018

OTHER PUBLICATIONS

European Patent Office, Partial Supplementary European Search Report dated Jun. 16, 2023 for European Patent Application No. 20831225.6.
(Continued)

*Primary Examiner* — Andargie M Aychillhum
(74) *Attorney, Agent, or Firm* — NORTON ROSE FULBRIGHT CANADA LLP

(57) ABSTRACT

An electronic textile system and a docking assembly for the electronic textile system. The system includes a textile substrate, an input device attached to the textile substrate, and a docking assembly attached to the textile substrate for removably receiving a controller device. The docking assembly includes a first electrical interface for mating with a second electrical interface of the controller device. The system includes an electrical conductive pathway network integrated in the textile substrate for electrically coupling the input device and the first electrical interface. The input device may transmit to the controller device electronic signals representing input data when the controller device is received by the docking assembly.

18 Claims, 38 Drawing Sheets

(58) Field of Classification Search
USPC .......................................................... 174/255
See application file for complete search history.

(56) References Cited

U.S. PATENT DOCUMENTS

| | | |
|---|---|---|
| 2012/0029299 A1 | 2/2012 | DeRemer et al. |
| 2012/0094528 A1* | 4/2012 | Vroom .................. H01R 13/73 |
| | | 439/540.1 |
| 2014/0071789 A1* | 3/2014 | Brodsky ................. G01S 15/89 |
| | | 367/7 |
| 2015/0072731 A1 | 3/2015 | Salmon |
| 2016/0113581 A1 | 4/2016 | Amir et al. |
| 2018/0307274 A1 | 10/2018 | Nakamura |
| 2018/0345015 A1 | 12/2018 | Straka et al. |

OTHER PUBLICATIONS

Patent Cooperation Treaty, International Search Report and Written Opinion dated Sep. 3, 2020 for International Application No. PCT/CA2020/050882.
European Patent Office, European Search Report dated Nov. 7, 2023 for European Patent Application No. 20831225.6.

* cited by examiner

ELECTRONICS-TO-TEXTILE INTERCONNECTION METHOD AND SYSTEM

CROSS REFERENCE TO RELATED APPLICATIONS

This disclosure claims priority from U.S. provisional patent application No. 62/868,560, entitled "ELECTRONICS-TO-TEXTILE INTERCONNECTION METHOD AND SYSTEM", filed on Jun. 28, 2019, the entire contents of which are hereby incorporated by reference herein.

TECHNICAL FIELD

The present invention relates in general to smart textiles. More specifically, the present invention relates to a method and system of connecting electronic components to electrically conductive textiles.

BACKGROUND

Smart textiles are a fabric based system of materials and structures that sense and react to environmental conditions or stimuli, such as those from mechanical, thermal, chemical, electrical, magnetic or other sources. Smart textiles can react or adapt to external stimuli or changing environmental conditions. The stimuli can include changes in temperature, moisture, pH, chemical sources, electric or magnetic fields, mechanical stress or strain.

Advanced smart textiles can have embedded computing, digital components, electronics, energy supply, and sensors. Basic components of smart textiles include sensors, actuators, data transmission and electrical power. When challenging functionality, size, cost, reliability, comfort and aesthetic/requirements are considered, there is an unmet need to seamlessly integrate electronic components into the manufacturing of the textiles. Further, electrical connections between electrically conductive circuits of the textiles (e.g. conductive fibres, wires, etc., of the textile substrate) with electronic components, such as power sources and computational components (e.g. processor, memory, etc.) require adaptable and/or reliable connection to the textiles.

Furthermore, textile manufacturing and electronics manufacturing use vastly different manufacturing infrastructures, utilizing highly dissimilar assembly equipment, materials and processes.

Hence, there is an urgent requirement for materials and manufacturing methods which can easily integrate the interconnection of electronics devices or electronics modules into textile based substrates.

SUMMARY

Electronic textile systems and docking assemblies are described herein.

In one aspect, an electronic textile system is provided. The electronic textile system may include: a textile substrate; an input device attached to the textile substrate; a docking assembly attached to the textile substrate for removably receiving a controller device, the docking assembly including a first electrical interface for mating with a second electrical interface of the controller device; and an electrical conductive pathway network integrated in the textile substrate for electrically coupling the input device and the first electrical interface, wherein the input device transmits to the controller device electronic signals representing input data when the controller device is received by the docking assembly.

In another aspect, a docking assembly for an electronic textile system is provided. The docking assembly may include: a docking base including a first electrical interface for mating with a second electrical interface of a controller device receivable by the docking assembly; and an engagement device adjustably positioned within the docking base in a receive position, the engagement device including a first magnet for interacting with a second magnet of the controller device to align the first electrical interface with the second electrical interface for establishing an electrical connection, and wherein the first magnet repels the second magnet for separating the first electrical interface from the second electrical interface upon movement of the engagement device away from the receive position within the docking base.

BRIEF DESCRIPTION OF THE DRAWINGS

The accompanying drawings, which are incorporated herein and form a part of the specification, illustrate the present invention and, together with the description, further explain the principles of the invention and to enable a person skilled in the pertinent art to make and use the invention.

DETAILED DESCRIPTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, specific details are set forth to provide a thorough understanding of the invention. However, it is understood that the invention may be practiced without these specific details. In other instances, well-known structures and techniques known to one of ordinary skill in the art have not been shown in detail in order not to obscure the invention. Referring to the figures, it is possible to see the various major elements constituting the apparatus of the present invention.

Figure 1:
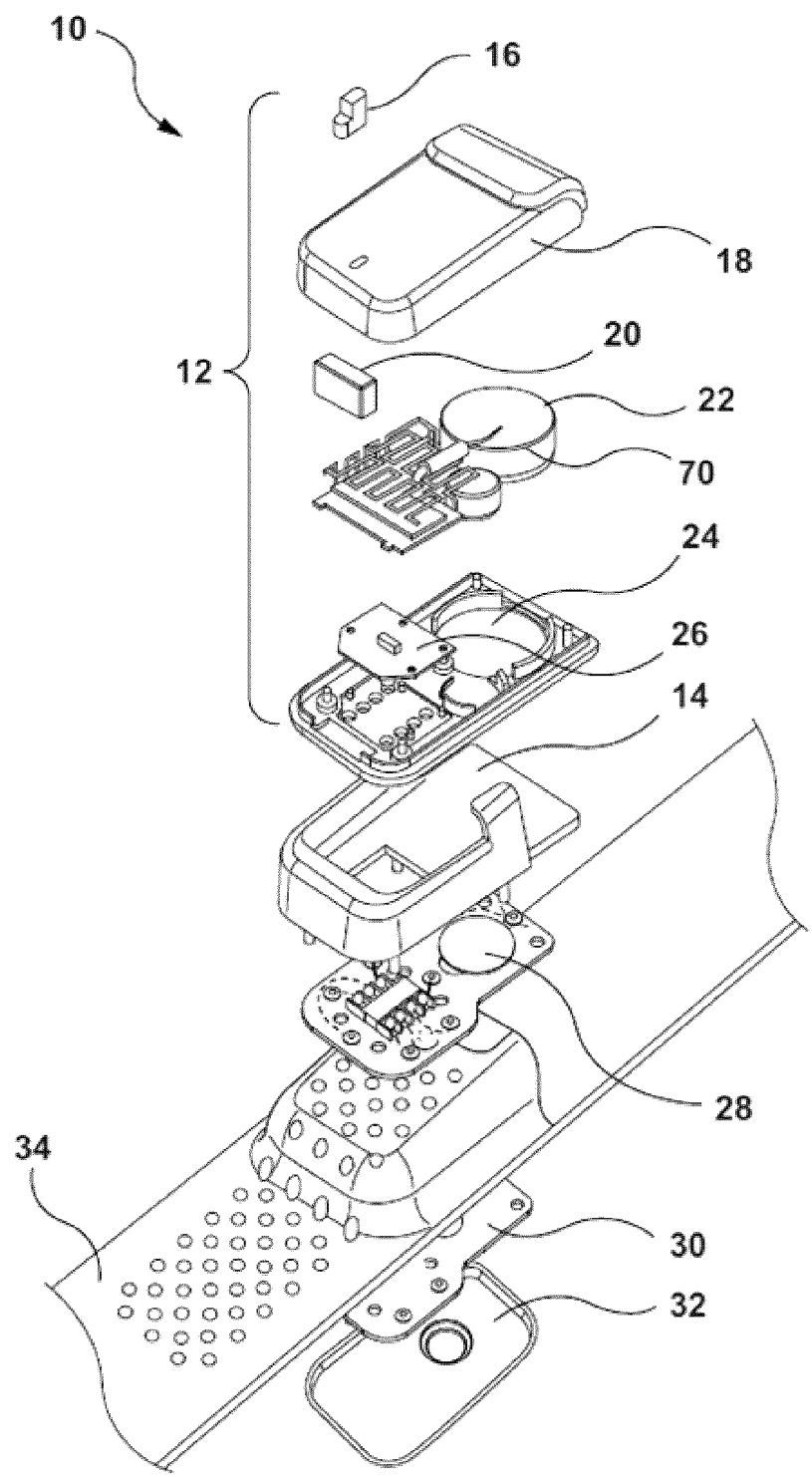
FIG. 1 illustrates a partial exploded perspective view of an electronic textile system, in accordance with an example embodiment of the present application.
Figure 4:
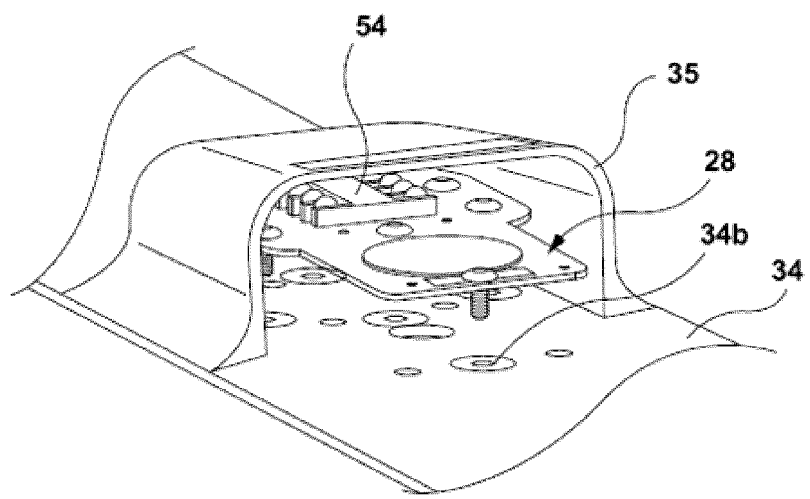
FIG. 4 illustrates a perspective view of the substrate component of FIG. 2 in relation to the textile substrate of FIG. 1.

Referring to FIG. 1, shown is an expanded (or exploded) view of an overall assembly 10 of a controller device 12 (e.g. electronic module) electrically connected to conductive pathways 80 (see FIG. 16) of a textile substrate 34 (e.g. in the form of a patch, band, shirt, pants, socks, undergarment, blanket, hat, glove, shoe, etc.) by way of a module dock station 14. As such, the module dock station 14 (see FIG. 5) can comprise a dock housing 50 having a body 14a with an aperture 52 for providing access between an electrical dock connector 54 (see FIG. 4) coupled to the conductive pathways 80 and an electrical controller connector 26 (see FIG. 1) that is connected to electronics 22 of the controller device 12, as further described below. The module dock station 14 can also have one or more clips 55 (as an example of a releasably securable mechanism for mechanically coupling with the housing 18,24 of the controller device 12). It is clear that the mating electrical connection between the electrical dock connector 54 and the electrical controller connector 26 is also releasably securable, thus facilitating repeated installation and removal of the controller device 12 with respect to the module dock station 14, both mechanically as well as electrically.

Periodic removal of the controller device 12 could be advantageous for recharging of a power source 70 (see FIG. 1) of the controller device 12, replacement/substitution of the controller device 12 (including the electronics 22), and/or temporary removal of the controller device 12 for washing/cleaning purposes of the textile substrate 34 (e.g. when washing a garment which integrally incorporates the textile substrate 34 as part of the overall garment construction).

Figure 6:
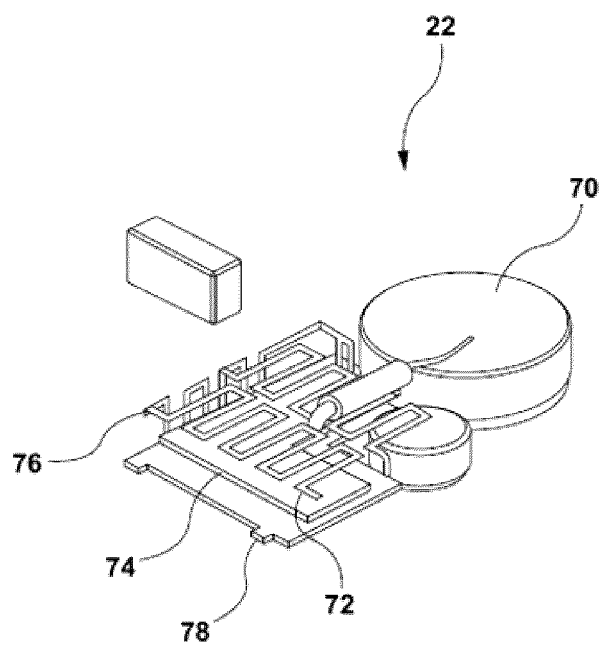
FIG. 6 provides an example embodiment of the electronic components of the controller device of FIG. 1.
Figure 7:
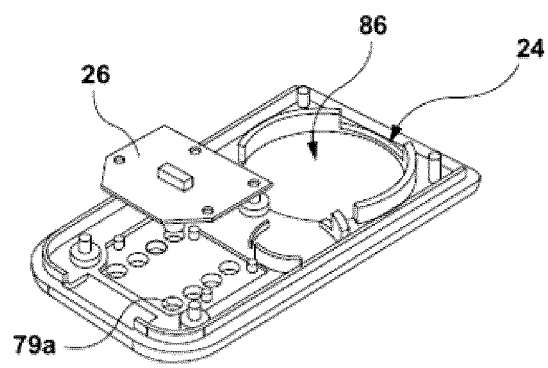
FIGS. 7 and 8 provide views of the interior of the controller device of FIG. 1.

Referring again to FIG. 1, the controller device 12 has a housing 18,24 (e.g. a top enclosure and a bottom enclosure) providing a moisture resistant housing for the enclosed electronics 22. For example, referring to FIG. 6, the electronics 22 can include a power source 70 (e.g. rechargeable battery) powering a memory 72 and a computer processor 74, such that the computer processor executes instructions store on the memory (e.g. ROM, RAM, etc.). The electrical connections between the electronics 22 can be by way of conductive pathways 76 (shown in concept) on a printed circuit board (PCB) or other electronics substrate 78. The conductive pathways 76 can be electrically connected to the electrical controller connector 26 (e.g. a socket connector—e.g. an 8 socket connector), such that the electrical controller connector 26 can be considered as integral within the housing 18,24 (see FIG. 7). As such, the electrical controller connector 26 can be considered as part of the controller device 12.

Figure 8:
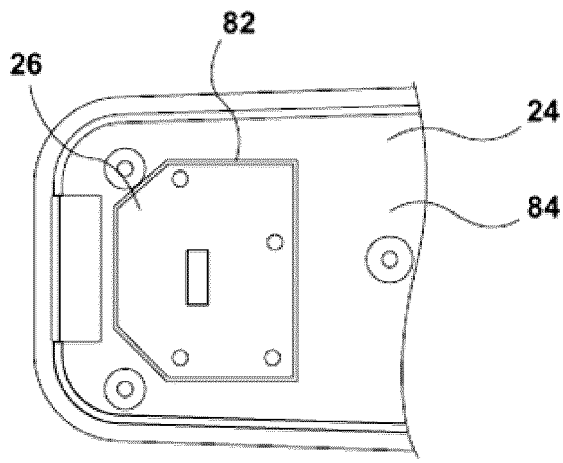

The bottom enclosure 24 of the housing can include apertures 79a for receiving corresponding pins 79b mounted on a body 54a of the electrical dock connector 54 (e.g. an 8 pin connector). It is also envisioned that the electrical dock connector 54 can be a socket connector and the electrical controller connector 26 can be a pin connector 26 configured for mating with the socket connector 54. It is also recognized that the electrical connectors 26,54 can have mating electrical connections other than of the pin/socket type (e.g. magnetic), as desired, in so much that the electrical connectors 26,54 are of the releasably securable type. As shown in FIG. 8, the electrical controller connector 26 can be sealed via a seal 82 (e.g. adhesive) with respect to an interior surface 84 (of the housing 18,24 when assembled). The seal 82 can be used to inhibit moisture or other foreign matter from entering into the interior 86 (see FIG. 7) via the apertures 79a (see FIG. 7).

Figure 2:
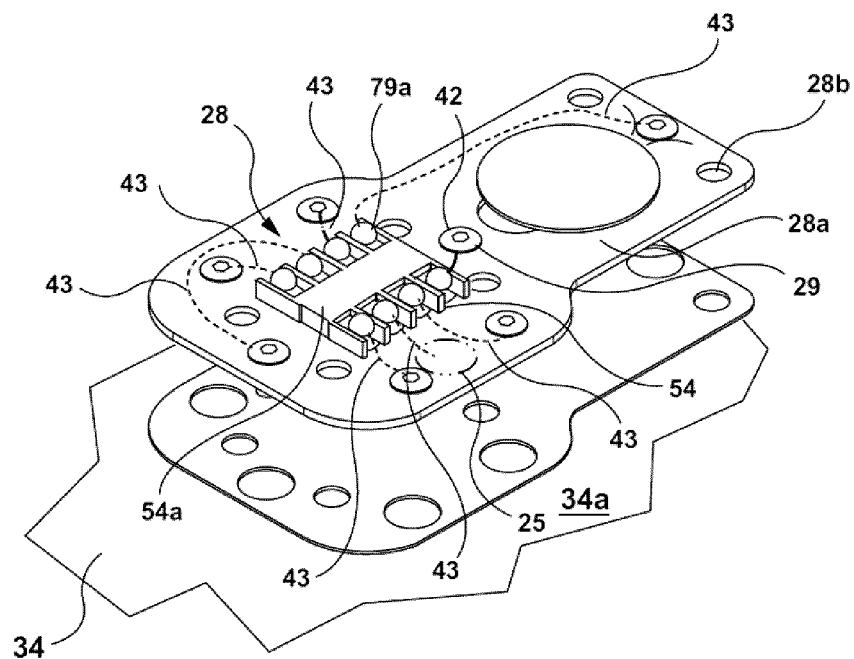
FIG. 2 illustrates a perspective view of a substrate component of the electronic textile system of FIG. 1.

Referring again to FIG. 1, the overall assembly 10 also includes a first substrate 28 and a second substrate 30 for mounting on either side of the textile substrate 34. For example, the first substrate 28 can be a PCB. As shown in FIG. 2, the first substrate 28 has the electrical dock connector 54 mounted thereon, with conductive pathways 43 connecting each of the one or more electrical connectors 79b (e.g. pins, sockets, etc.) of the electrical dock connector 54 with corresponding one or more electrical connection locations 42 mounted on the first substrate 28. It is recognized that the one or more electrical connection locations 42 can be distributed about a surface 28a of the first substrate 28, such that each of the locations of the one or more electrical connection locations 42 correspond (e.g. in relative distance from one another) with the conductive pathways 80 (see FIG. 16) laid out on/in the textile substrate 34. The first substrate 28 can also have one or more electrical components 25 mounted thereon and thus electrically connected to the electronics 22 via the mated connectors 26,54 (pins/sockets) via corresponding conductive pathway(s) 43. As shown, the first substrate 28 can have a plurality of apertures 28b corresponding in spatial distribution with the spatial distribution of holes 34b of the textile substrate 34 (see FIG. 4). The apertures 28b are also matching in spatial distribution with a series of apertures 30b of a surface 30a of the second substrate 30 (e.g. a PCB). In assembly of the overall assembly 10, the first substrate 28 can be mounted on a corresponding surface 34a of the textile substrate 34 by an adhesive layer A. In assembly of the overall assembly 10, the second substrate 30 can be mounted on a corresponding opposing surface 34a of the textile substrate 34 by a similar adhesive layer A.

Figure 3:
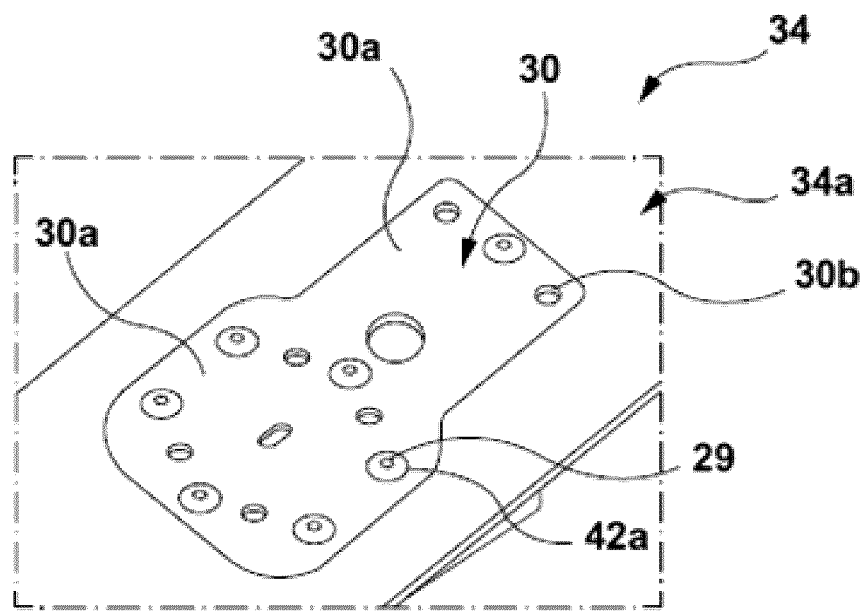
FIG. 3 illustrates a perspective view of a substrate component of the electronic textile system of FIG. 1, in accordance with another example embodiment of the present application.

Referring to FIG. 3, the second substrate 30 is mounted on an opposite surface 34a of the textile substrate 34 to that used to mount the first substrate 28, such that the textile substrate 34 is securely fastened between the substrates 28, 30, as further described below. The second substrate 30 also has connection locations 42a corresponding to the electrical connection locations 42, such that corresponding mechanical fasteners 29 (e.g. rivets—see FIG. 2) can be used to mechanically fasten the first substrate 28 to the second substrate 30, thus fixedly sandwiching/mounting the textile substrate 34 there-between).

Figure 5:
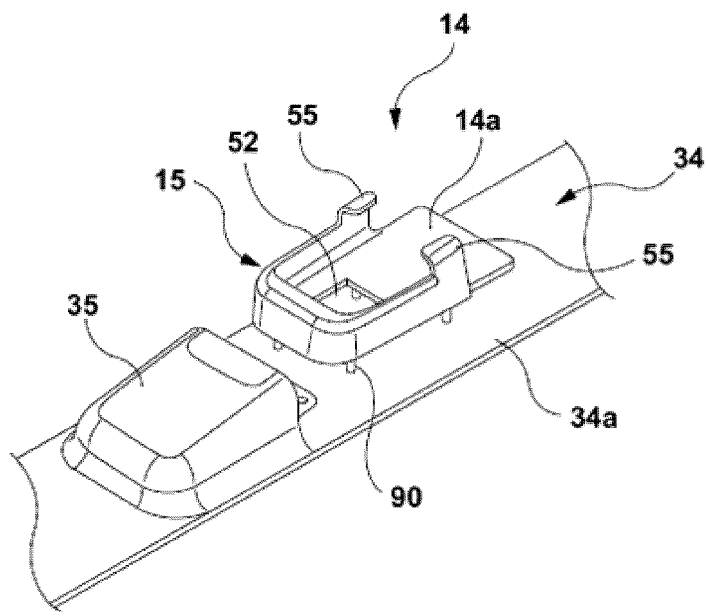
FIG. 5 illustrates a perspective view of a dock station body of FIG. 1 in relation to the textile substrate of FIG. 1.

Referring again to FIG. 4, an optional pocket 35 of the textile substrate 34 can be used to house the first substrate 28, as desired. As can be seen in FIG. 5, the optional pocket 35 can also be used to house the module dock station 14, when fastened to the first substrate 28 (further described below). Referring again to FIG. 1, the second substrate 30 can be covered by an optional backing 32 (e.g. fabric, plastic, padding, laminate, etc.) material, so as to provide for comfort of the wearer of the textile substrate 34 (e.g. as incorporated into a garment), when the backing 32 material is in contact with a skin of the wearer. The overall assembly 10 can also include a light pipe 16 (for indicating functional status of the electronics 22 via one or more visual indicators (e.g. LEDs) as well as a positioned magnet 20 in the interior 86 of the housing 18,24. In summary, the housing 18,24 of the controller device 12, once assembled, can be releasably secured, both mechanically and electrically, with the module dock station 14. The module dock station 14 is fixedly attached to the first substrate 28, which is in term fixedly attached to the textile substrate 34 via the mechanical (e.g. fasteners)/chemical (e.g. adhesive) connection between the first substrate 28 and the second substrate 30 when positioned on opposed sides 34a of the textile substrate 34.

Figure 9:
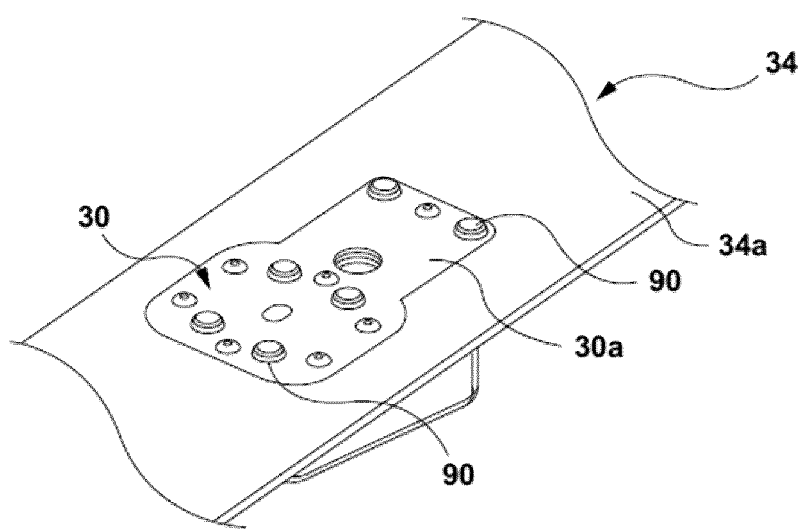
FIGS. 9, 10, 11 provide views of the substrate component of FIG. 3 in relation to the textile substrate of FIG. 1.
Figure 15:
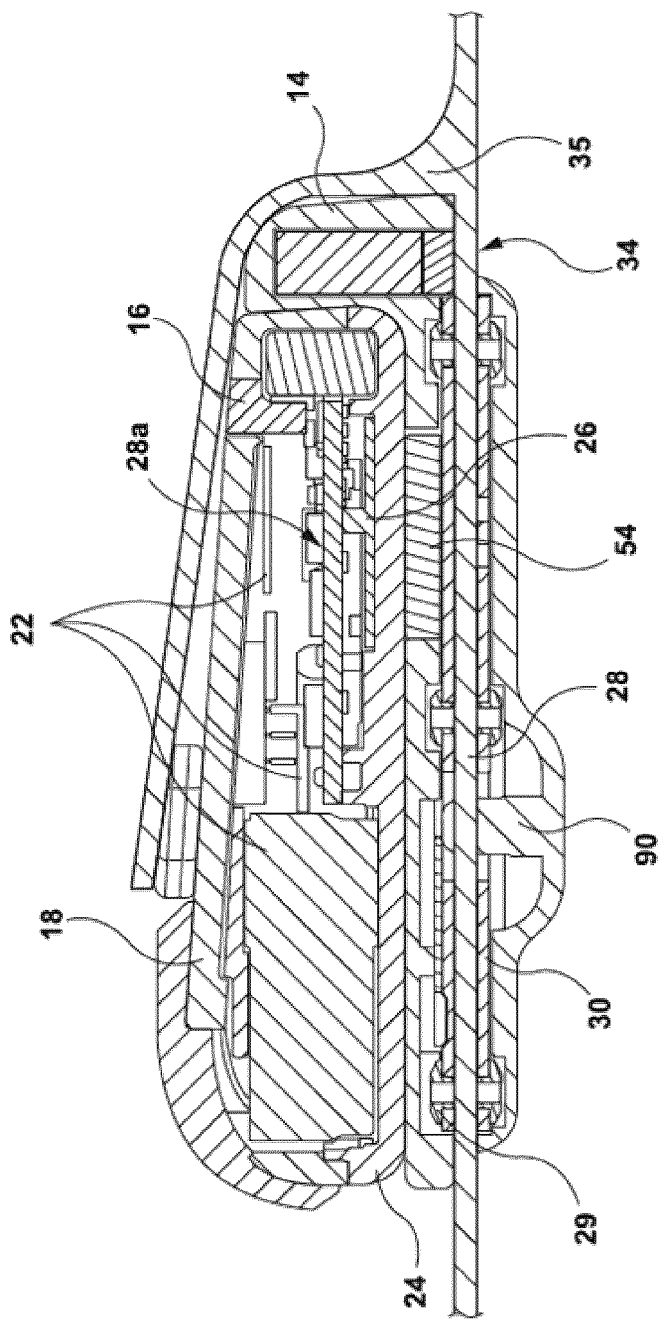
FIG. 15 illustrates a cross-sectional view of the entire overall assembly of FIG. 1 after assembly.

Referring again to FIGS. 2, 3, 4, the apertures 28b, 30b and holes 34b can be used to fasten the module docking station 14 with the substrate(s) 28,30 to one another, thus fixedly securing the module docking station 14 to the textile substrate 34. For example, one fastening method of the module docking station 14 with the substrate(s) 28,30 can be using a staking method (see FIGS. 5, 9, 15), whereby staking is the process of connecting the two components (the module docking station 14 with the substrate(s) 28,30) by creating an interference fit of a fastener 90 between the two pieces (the module docking station 14 with the substrate(s) 28,30). One workpiece 28,30 has a hole 28b,30b in it while the other (the module docking station 14) has a boss 90 that fits within the hole 28b,30b. It is recognized that one of the workpieces 28, 30 can have the respective hole(s) 28b, 30b while the other of the pieces (the module docking station 14) can have the fastener(s) 90 mounted on the corresponding surface 28a,30a. The fastener 90 (e.g. boss) can be very slightly undersized so that it forms a slip fit with the hole 28b,30b. A staking punch can then be used to expand the boss 90 radially and to compress the boss 90 axially so as to form an interference fit between the workpieces (the module docking station 14 with the substrate(s) 28,30). This interference fit forms a permanent join(s)/connection(s) between the two pieces, such that the interposed textile substrate 34 is fixedly secured between the two substrates 28,30 which in turn is fastened to the module docking station 14 via the staking. The staking process can also be referred to as thermoplastic staking, also known as heat staking, which is the same process except that it uses heat to deform the plastic boss 90, instead of cold forming. A plastic stud 90 protruding from one component fits into a hole in the second component. The stud 90 is then deformed through the softening of the plastic to form a head which mechanically locks the two components (the module docking station 14 with the substrate(s) 28,30) together. Unlike welding techniques, staking has the capacity to join plastics to other materials (e.g. metal, PCB's) in addition to joining like or dissimilar plastics, and it has the advantage over other mechanical joining methods in reducing the need for consumables such as rivets and screws.

Figure 10:
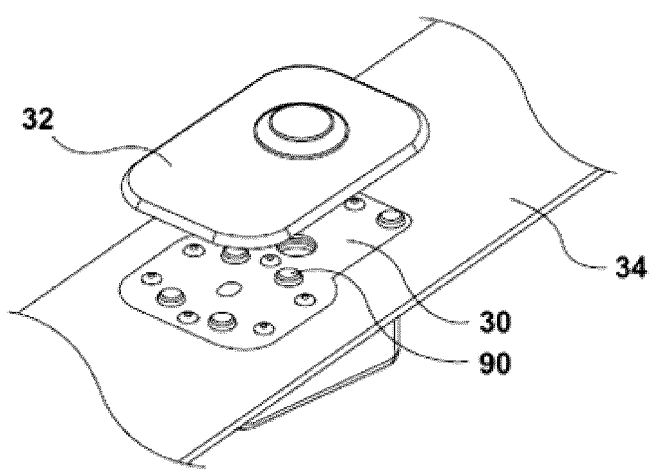
Figure 11:
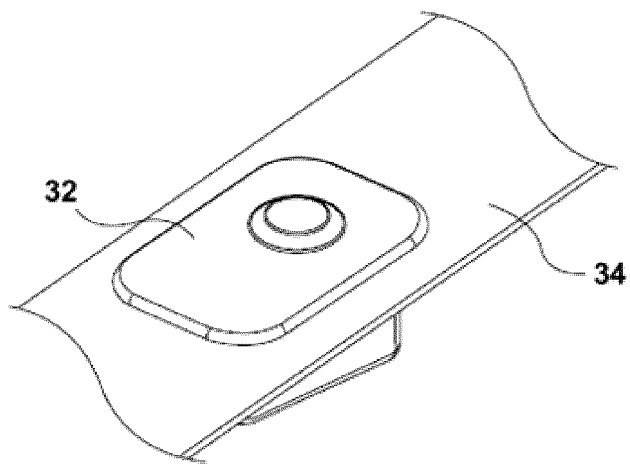
Figure 12:
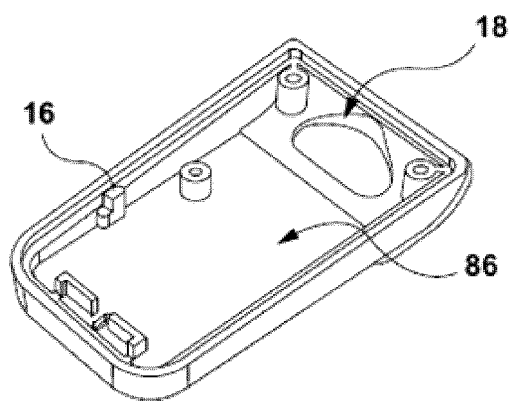
FIGS. 12, 13, 14 provide views of the controller device of FIG. 1 in both assembled and unassembled.
Figure 13:
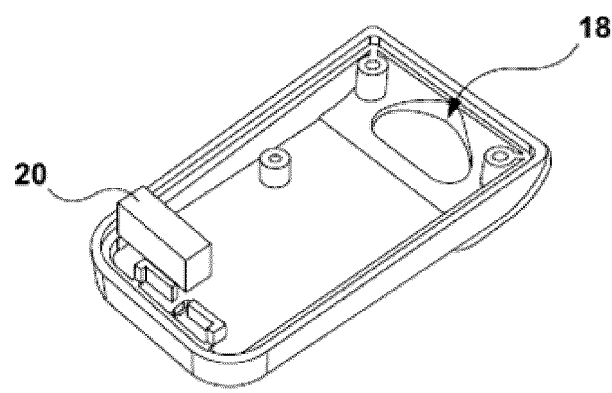
Figure 14:
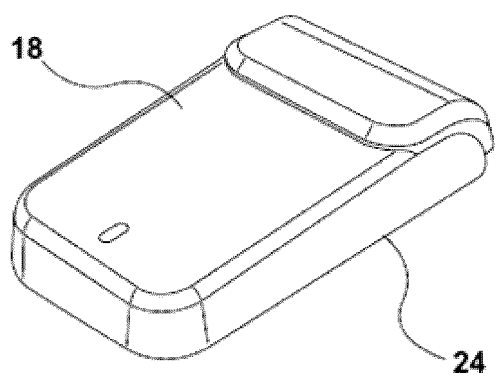
Figure 16:
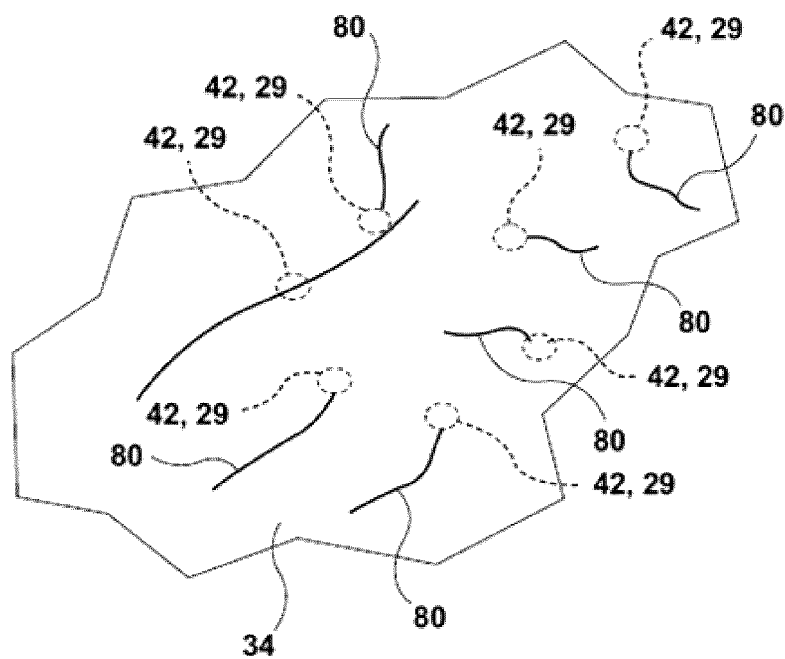
FIG. 16 is an example view of the textile substrate of FIG. 1 including conductive pathways.

Referring to FIGS. 10 and 11, shown is an example backing 32 in order to cover the second substrate 30 after being fastened to the first substrate 28. Referring to FIGS. 12, 13, 14, shown is the housing 18,24 in an unassembled and assembled form, such that the interior 86 with mounted light pipe 16 and magnet 20 are shown by example. Referring to FIG. 16, shown is a cross sectional view of the overall assembly 10, including an optional piezo sensor mounted between the first substrate 28 and the body 14a of the module dock station 14.

Referring to FIG. 16, shown is an example textile substrate 34 with the conductive pathways 80, as an illustration only, with the locations of the electrical connector locations 42 (and/or fasteners 29) of FIG. 2 in ghosted view. It is recognized that an electrical connection between the electrical connector locations 42 and the conductive pathways 80 is fixed when the electrical connector locations 42 (of the first substrate 28) come into contact with the conductive pathways 80, which is maintained due to 1) the fixed connection (e.g. via fasteners 90) between the substrates 28,30 thus sandwiching the textile substrate 34 there between and biasing the electrical connectors locations 42 and the conductive pathways 80 into physical contact with one another; and/or 2) the connection via the fasteners 29

(e.g. conductive fasteners such as metal rivets, pins, etc.) between the substrates 28,30 as the fasteners 29 are in physical contact with the electrical pathways 80 as well as the electrical connector locations 42. The substrates 28,30 can be made of flexible or rigid material, as desired, so long as the material retains the interconnection between the locations 42 by the fasteners 29.

For example, electrical current to the electronics 22 follows the electrically conductive path of: a) from the conductive pathways 76 to b) the electrical controller connector 26 to c) the electrical dock connector 54 to d) the conductive pathways 43 connecting each of the one or more electrical connectors 79b (e.g. pins, sockets, etc.) of the electrical dock connector 54 to e) corresponding one or more electrical connection locations 42 to finally f) (e.g. via the fasteners 29) positioned adjacent to and electrically bonded to the conductive pathways 80 of the textile substrate 34. Similarly, electrical current from the conductive pathways 80 of the textile substrate 34 follows the electrically conductive path of: a) (e.g. via the fasteners 29) positioned adjacent to and electrically bonded to the conductive pathways 80 of the textile substrate 34 to b) corresponding one or more electrical connection locations 42 to c) the conductive pathways 43 connecting each of the one or more electrical connectors 79b (e.g. pins, sockets, etc.) of the electrical dock connector 54 to d) the electrical dock connector 54 to e) the electrical controller connector 26 to f) the conductive pathways 76 connected to the electronics 22.

Figure 17:
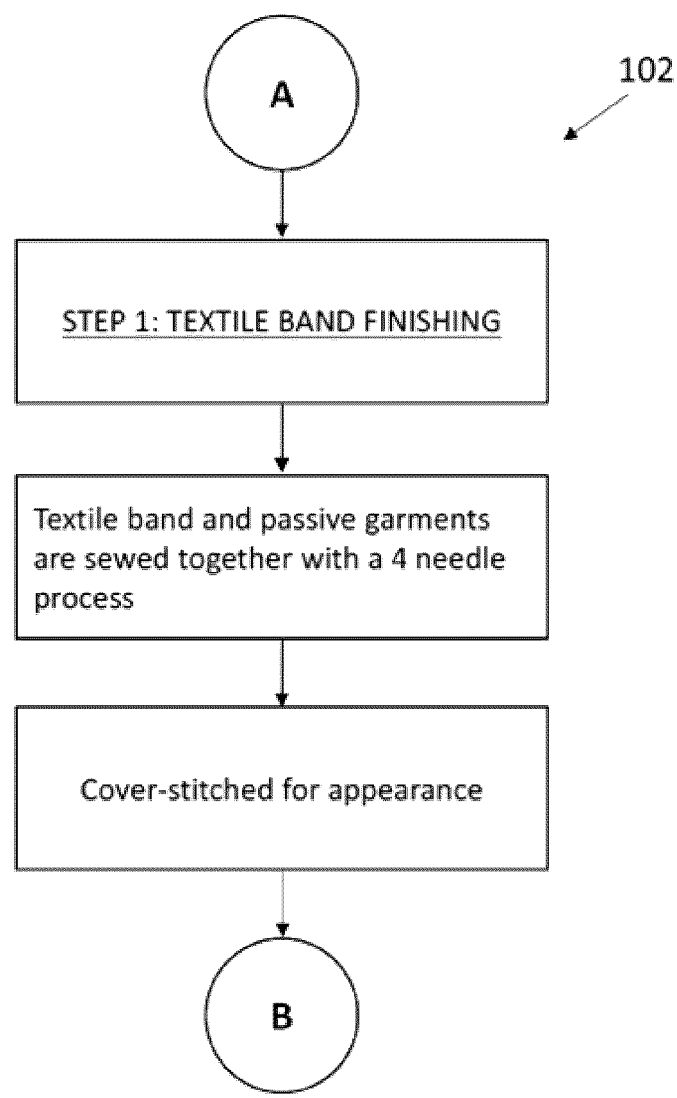
FIGS. 17-21 are example flowcharts of assembly methods for the overall assembly of FIG. 1.
Figure 18:
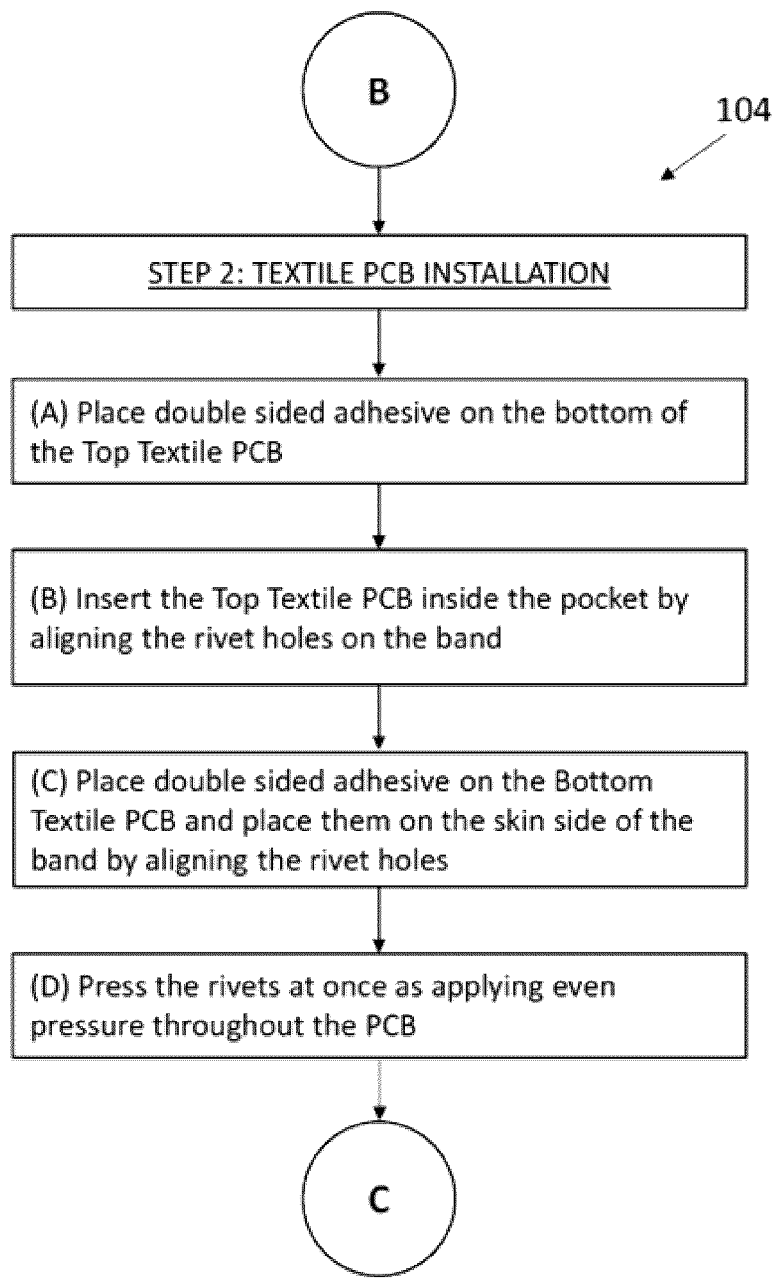
Figure 19:
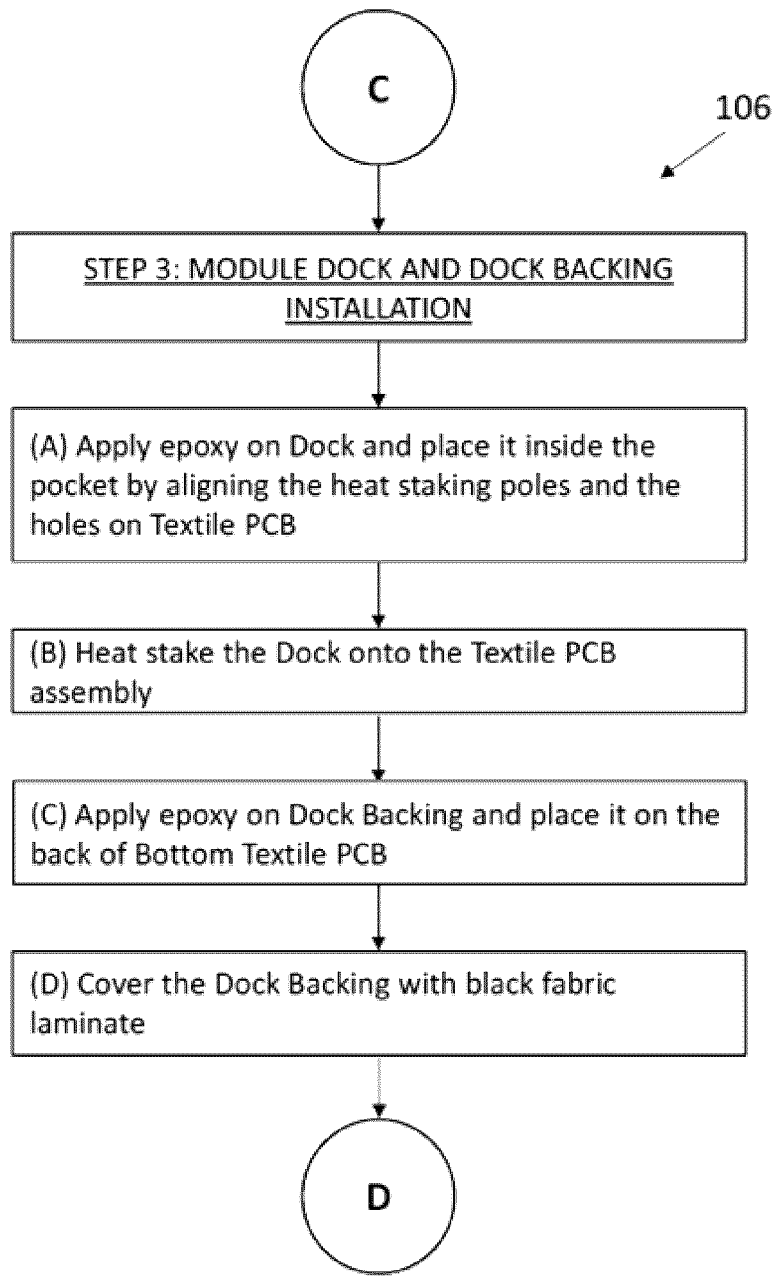
Figure 20:
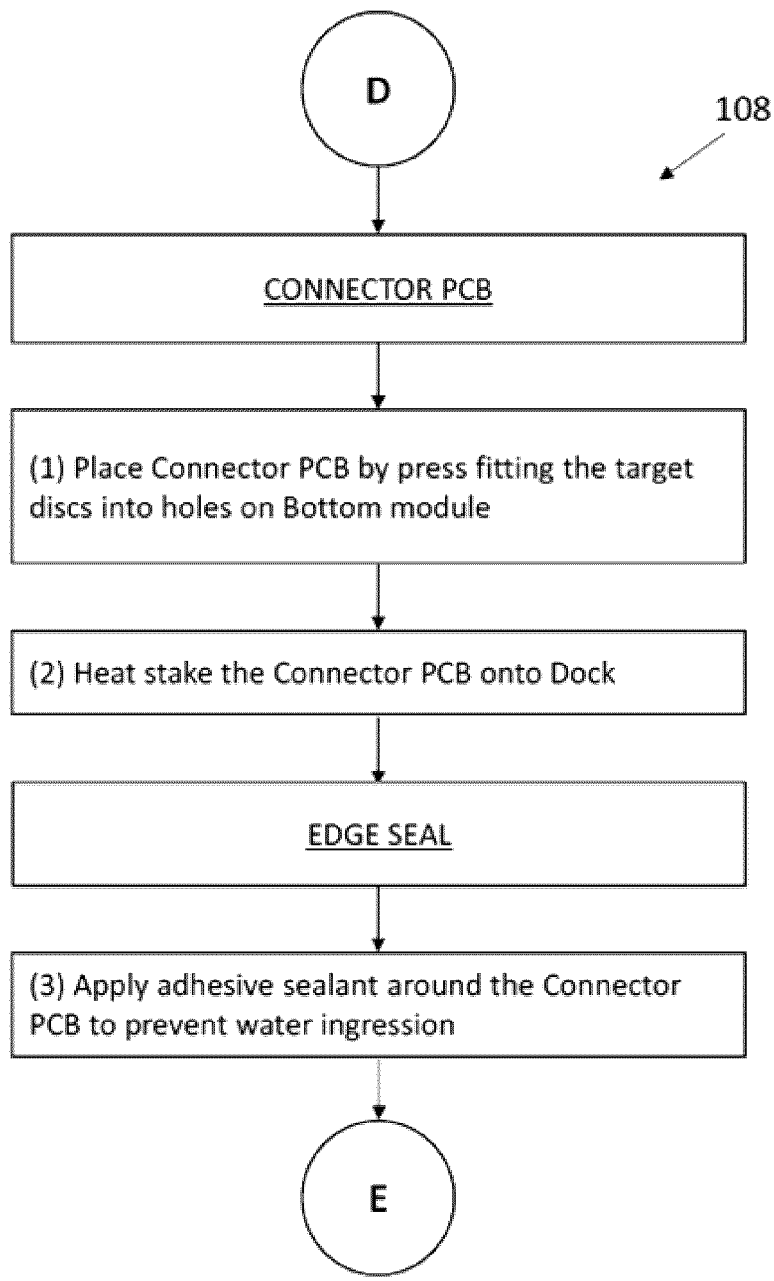
Figure 21:
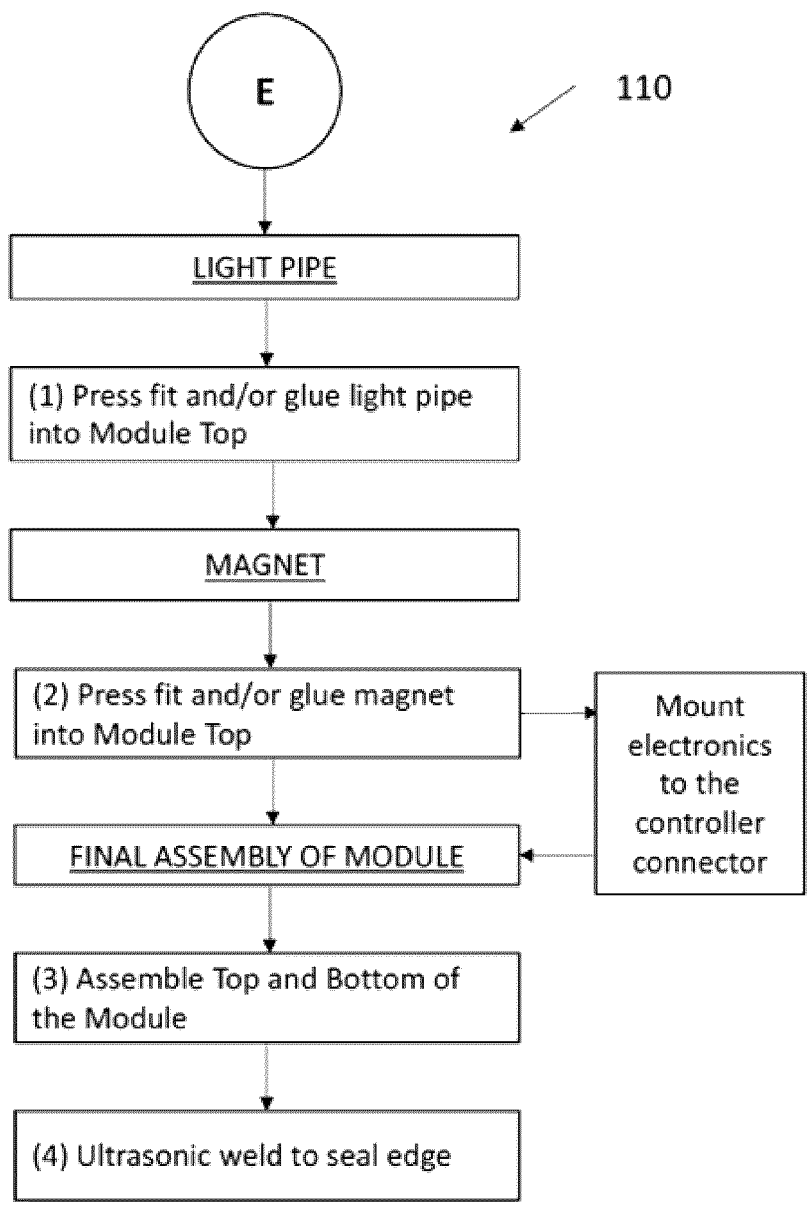

In fabrication of the overall assembly 10, the following example manufacturing processes can be performed. FIG. 17 shows an example process 102 for manufacture of the textile substrate 34 including the conductive pathways 80 (e.g. circuits containing conductive wires/fibres with attached sensors/actuators applied on or otherwise interlaced, knit/woven, with the fibres of the textile substrate 34). FIG. 18 shows an example method steps 104 to manufacture the sandwich of the two substrates 28,30 with the textile substrate 34. Referring to FIG. 19, shown is a method 106 to fasten (e.g. mechanical) the module docking station 14 to the first substrate 28 underlying and adjacent to the module docking station 14. Further, the backing 32 is fastened (e.g. adhesive) to the second substrate 30 underlying and adjacent to the backing 32. FIG. 20 is an example manufacture 108 of the electrical controller connector 26 onto the housing 18,24 of the controller device 12. FIG. 21 is a method of manufacture 110 for the main controller device 12, including mounting of the components 16, 20, 22 within the interior 86 of the housing 18,24 and sealing the housing 18,24.

As shown above by example, the overall assembly 10 included the controller device 12, the module dock station 14 fixedly connected to the substrate(s) 28,30, and the substrates 28,30 fixedly connected to the textile substrate 34 (having the plurality of conductive pathways 80). As such, the controller device 12, once assembled, is both mechanically and electrically releasably securable to the module dock station 14, in order to effect electrical communication between the electronics 22 of the controller device 12 and the conductive pathways 80 of the textile substrate 34.

Accordingly, described by example only is: (a) light pipe 16, (b) top enclosure 18, (b) magnet 20, (c) main electronics 22 which can contain (d) the main PCB 28, (e) battery 70 and (f) other electronic components 72,74,76, (g) bottom enclosure 24, which holds (h) the connector PCB 26, (i) module dock 14, (j) top textile PCB 28 which are located above the (j) textile band 34 and under the (k) textile pocket 35 and the (l) bottom textile PCB 30 and (m) fabric and laminate padding 32, which are located below the textile band 34.

Further, the embodiments comprise apparatus and methods to make a reliable interconnection between electronic devices 12 and smart textiles 34. The embodiments facilitate the electronic device 12 to maintain a robust electrical connection to electrically conductive circuits 80 on the smart textile 34 while also being securely mechanically fastened to the smart textile 34, thus acquiring the ability to withstand mechanical shock, torsion, stretch and other stresses to which the smart textile 34 or electronic devices 12 may be subject to.

In some embodiments the textile band 34 or textile substrate 34 may contain no electrical or electronic components. In some embodiments, the textile substrate 34 may contain only electrically conductive circuits 80, such as electrically conductive yarn, fiber or printed electronic circuits. In other embodiments, the textile substrate 34 may contain fully functional and active electronic components, sensors, circuits and the like.

For the purposes of a wearable smart textile 34 worn on the body, the direction of below the textile band 34 would be interpreted as being closer to the body and above the textile band 34 would be farther away from the body. The textile pocket 35 is preferably a structure which is raised above the textile band 34 and fabricated by knitting into the textile band 34 knit structure.

In some embodiments, the textile substrate 34 (also called the textile band 34) has successfully incorporated health monitoring sensors in the form of ECG sensor pads, respiratory monitoring sensors and bio-impedance monitoring sensors. These sensors are electrically connected to conductive circuits 80 within the textile band 34, which are then connected using rivets 29, eyelet or grommets 42 leading to the hard electronics 22 (e.g. mounted on the PCB 78). In other embodiments, the main electronics PCB 78 has also successfully incorporated motion sensors and temperature sensors onto the module PCB 78, as part of the electronics 22.

FIG. 17 illustrates embodiment comprising textile form factors to which the textile substrate 34 has been successfully applied, including: underwear, bra and shirts. It can be appreciated that the embodiments are applicable to any form of textile substrate 34 or flexible substrate 34 exhibiting similar properties to a textile or fabric.

FIG. 18 illustrates the steps relating to assembling the top textile PCB 28 onto the textile band 34 with this embodiment comprising steps, including: (1) Placing an adhesive material A on the bottom side of the top textile PCB 28, (2) Inserting the top textile PCB 28 inside the textile pocket 35 by aligning the holes 42 on the top textile PCB 28 to the matching pre-punched rivet holes 34b onto the textile band 34, (3) Placing double-sided adhesive A on the bottom textile PCB 30 and placing it on the opposite side 34a of the textile band 34 to the top textile PCB 28, also aligning to the pre-punched rivet holes 34b in the textile band 34, and (4) Pressing the rivets 29 at the same time as applying even pressure to the PCBs 28,30.

Steps 1-4, above, create a robust and secure mechanical and electrical connection between the top textile PCB 28, the bottom textile PCB 30 and the textile band 34. In regions where an electrical connection is required, the pre-punched rivet holes 34b in the textile band 34 can be located such that an electrical conductive circuit 80 in the textile band 34 is physically in contact with the metal rivet 29 an/or the conductive locations 42 (e.g. part of the conductive pathways 43 positioned on the underside of the first substrate 28 (and thus able to be placed into direct contact with the surface 34a of the textile substrate 34). It should be noted that rivet 29 can also mean eyelet, grommet or similar type of metal fastening method.

The textile band pocket 35, which is fabricated in such a manner as to be raised above the surface 34a of the textile band 34 facilitating just enough room for the module dock housing 50 to fit snugly within the pocket 35, while also facilitating it to be removed when necessary.

FIG. 19 illustrates the steps 106 relating to assembling the module dock 14 and dock backing 32 into the textile band 34, with this embodiment comprising steps, including: (1) Applying epoxy to the dock 14 and placing it inside the pocket 35 by aligning the heat stacking poles 90 to the holes 28b,30b on the textile PCBs 28,30, (2) Heat staking the dock 14 onto the textile PCB 28,30,34 assembly, (3) Applying epoxy to the dock backing 32 and placing it on the back of the bottom textile PCB 30, and, (4) Covering the dock backing 32 with a fabric, preferably laminated.

FIG. 20 illustrates the steps 108 relating to assembling the connector PCB 26 into the bottom module enclosure 24 with this embodiment comprising the steps of: (1) placing and press-fitting the connector PCB target discs 26 into the bottom module holes 79a, (3) heat staking the connector PCB 26 onto the dock body 14a, (4) applying adhesive sealant around the connector PCB 26 to prevent water ingression between the body 14a and the connector 26.

FIG. 21 illustrates the steps 110 relating to assembling the light pipe 16 and magnet 20 and corresponding electronics 22 into the module top enclosure 18 and assembling the top 18 and bottom 24 module enclosures together with this embodiment comprising the steps of: (1) Press fitting and/or gluing the light pipe 16 into Module Top 18, (2) Press fitting and/or gluing the magnet 20 into Module Top 18 as well as connecting the electronics 22 (e.g. via the PCB 78 together with the connector 26) in order to electrically connect the conductive pathways 76 of the electronics 22 with the connectors of the connector 26), (3) Assembling the Top 18 and Bottom 24 of the Module 12 together, and (4) Ultrasonically welding to seal the edges of the top 18 and bottom 24 module.

Other options for manufacture can include generally processes such as but not limited to:

1) the process of assembly comprises the steps of: assembling the top textile PCB onto the textile band; placing an adhesive material on the bottom size of the top textile PCB; inserting the top textile PCB inside the textile pocket by aligning the holes on the top textile PCB to the matching pre-punched rivet holes onto the textile band; placing double-sided adhesive on the bottom textile PCB and placing it on the opposite side of the textile band to the top textile PCB, also aligning to the pre-punched rivet holes in the textile band; and pressing the rivets at the same time as applying even pressure to the PCBs;

2) in regions where an electrical connection is needed, the pre-punched rivet holes in the textile band can be located such that an electrical conductive circuit in the textile band is physically in contact with the metal rivet;

3) the textile band pocket can be fabricated in such a manner as to be raised above the surface of the textile band providing just enough room for the module dock housing to fit snugly within the pocket, while also allowing it to be removed when used;

4) assembling the module dock and dock backing into the textile band; applying epoxy to the dock and placing it inside the pocket by aligning the heat stacking poles to the holes on the textile PCBs; heat staking the dock onto the textile PCB assembly; applying epoxy to the dock backing and placing it on the back of the bottom textile PCB; and covering the dock backing with a fabric, preferably laminated;

5) assembling the connector PCB into the bottom module enclosure; placing and press-fitting the connector PCB target discs into the bottom module holes; heat staking the connector PCB onto the dock; and applying adhesive sealant around the connector PCB to prevent water ingression; and/or 6) assembling the light pipe and magnet into the module top enclosure and assembling the top and bottom module enclosures together; press fitting and/or gluing the light pipe into Module Top; press fitting and/or gluing the magnet into Module Top; assembling the Top and Bottom of the Module together; and ultrasonically welding to seal the edges of the top and bottom module.

Figure 22:
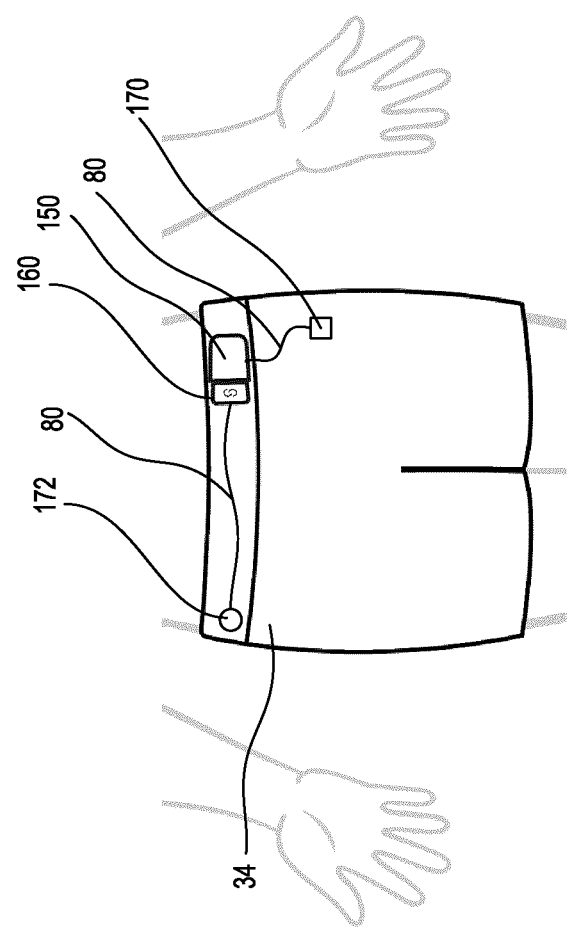
FIG. 22 illustrates an electronic textile system, in accordance with an example embodiment of the present application.

Reference is made to FIG. 22, which illustrates an electronic textile system including a textile substrate 34, a docking assembly 150 and a controller device 160, in accordance with an example embodiment of the present application. In FIG. 22, the textile substrate 34 may be an undergarment, such as a boxer brief undergarment. It may be appreciated that other types or shapes of undergarments may be contemplated. Further, the textile substrate 34 may be other types of garments, such as shirts, pants, shorts, hats, socks, undergarments, shirts, pants, shoes, gloves, headbands, belts, brassieres, balaclavas, base layers, jackets, sweatshirts, or outerwear. Other examples of textile substrates 34 may be contemplated.

In some embodiments, the docking assembly 150 may be the module docking station 14 (FIG. 1) described herein and may include the associated electrical dock connector 54 (FIG. 4), the first substrate 28 (FIG. 1), or the second substrate 30 (FIG. 1) described herein. In some embodiments, the docking assembly 150 may be provided by other example structures, as will be described herein.

In FIG. 22, the docking assembly 150 may be attached to the textile substrate 34 on the undergarment waistband. In other embodiments, the docking assembly 150 may be attached to the textile substrate at any other position of the textile substrate 34. The docking assembly 150 may be attached to the textile substrate 34 for removably receiving the controller device 160. The docking assembly 150 may include a first electrical interface for mating with a complementary second electrical interface of the controller device 160.

In some embodiments, the electronic textile system may include an input device 170 attached to the textile substrate 34. The input device 170 may be one or more sensors, such as a temperature sensor, a moisture sensor, a respiratory monitoring sensor, a heart rate sensor, an accelerometer, a gyroscope, an electroencephalogram (EEG) sensor, electromyography (EMG) sensor, an electrocardiography (ECG) sensor, a photoplethysmography (PPG) sensor, a ballistocardiograph (BCG) sensor, a galvanic skin response (GSR) sensor, a bio-impedance sensor (or bio-electrical impedance sensor), or chemical sensors (e.g., chemical sensors for sweat, glucose, urine, or the like).

Although one input device 170 is illustrated in FIG. 22, the electronic textile system may include any number of input devices positioned at various positions about the textile substrate 34.

In some embodiments, the electronic textile system may include an output device 172 attached to the textile substrate. For instance, the output device 172 may be an actuator. In some embodiments, the output device 172 may be a heating element, a haptic feedback element, a stimulation element, a visual display element, drug or substance delivery element, or the like. Stimulation elements may include electrical stimulation devices, mechanical stimulation devices, aural stimulation devices, or other types of devices for providing output to the user. In some embodiments, the output device 172 may provide feedback to a user of the electronic textile system, in response to data from the input device 170 or signals provided by the controller device 160. Although one output device 172 is illustrated in FIG. 22, the electronic textile system may include any number of output devices positioned at any other position about the textile substrate 34.

The electronic textile system includes an electronic conductive pathway network integrated in the textile substrate 34 for electrically coupling the input device 170, the output device 172, and/or the docking assembly 150. Accordingly, when the controller device 160 is received by the docking assembly 150, the controller device 160 may be electrically coupled to the input device 170 or the output device 180 via one or more conductive pathways 80. The one or more conductive pathways 80 may include conductive wires or fibers interlaced, knit, or woven with the textile substrate 34.

In some embodiments, when the controller device 160 is received by the docking assembly 150, the controller device 160 may receive signals representing data generated by the input device 170. Further, the controller device 160 may transmit signals representing instructions to activate the one or more output device 172 for providing feedback to a user of the textile substrate 34 (e.g., clothing).

In some embodiments, the controller device 160 may include an electrical power source, such as a battery. In some embodiments, the battery may be a removable or replaceable battery. In some embodiments, the battery may be a rechargeable battery, such as a lithium-ion battery. When the controller device 160 is received by the docking assembly 150, the controller device 160 may operate as a power source for supplying electrical power to the input device 170 or the output device 172. In some embodiments, the electrical power may be in the form of electrical current. In some other embodiments, the electrical power may be delivered via a wireless power delivery system, such as an inductive charging system.

In some embodiments described herein, the controller device 160 may be removably positioned within the docking assembly 150 such that the controller device 160 may be decoupled from the textile substrate 34 (e.g., clothing). This may be convenient, for example, when the electrical power source needs to be re-charged or replaced or when the textile substrate 34 may need to be washed.

Referring again to FIG. 1, the controller device 12 may be inserted into the module docking station 14 (FIG. 1) by sliding the module docking station 14 into the body 14a (FIG. 5) of the dock housing. The body 14a may provide structural support for retaining the controller device 12 within the module docking station 14. In FIG. 1, an electrical interface of the controller device 12 may be slid into contact with the electrical dock connector 54 (FIG. 4) for establishing an electrical connection between the controller device 12 and the electronic conductive pathway network integrated in the textile substrate 34.

In some embodiments, the controller device 12 may include a magnet 20 for attracting a magnet within the module docking station 14 to align the electrical interface of the controller device 12 with the electrical dock connector 54. The magnetic attraction forces may retain the controller device 120 within the module docking station 14.

In embodiments of the foregoing description with reference to FIG. 1, a controller device may be slidably inserted within a docking assembly. The controller device may be mechanically retained within the docking assembly based on magnetic forces from magnet components for establishing an electrical connection between the controller device and an electronic conductive pathway network integrated in a textile substrate. In some other embodiments, other docking assemblies and controller assembly structures may be contemplated.

Figure 23:
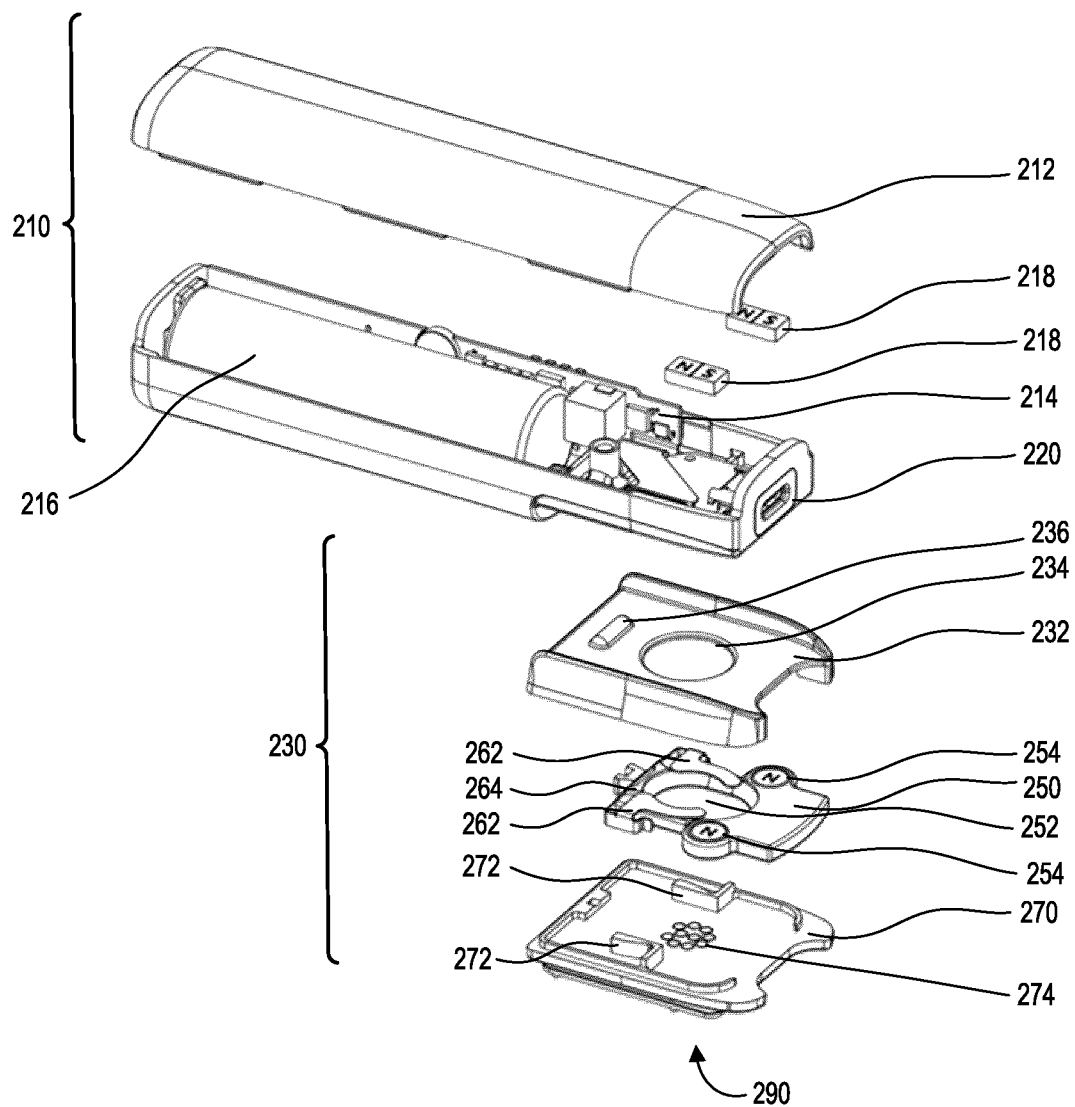
FIG. 23 illustrates an exploded top perspective view of an electronic controller device and a docking assembly, in accordance with an example embodiment of the present application.

Reference is made to FIG. 23, which illustrates an exploded top perspective view of an electronic controller device 210 and a docking assembly 230, in accordance with an example embodiment of the present application. The docking assembly 230 may be coupled to a textile substrate (not illustrated in FIG. 23). In some embodiments, the docking assembly 230 may be affixed to the textile substrate using adhesive. Other methods of affixing the docking assembly 230 to the textile substrate may be contemplated.

Textile substrates may include shirts, pants, socks, undergarments, blankets, hats, shoes, or other forms of clothing. A textile substrate may include a network of electrical conductive pathways for interconnecting sensors, actuators, or the like embedded with or integrated into the textile substrate. For example, the network of electrical conductive pathways may include one or more conductive wires or fibers that can be interlaced, knit/woven, or integrated into the fibers of the textile substrate. Accordingly, the docking assembly 230 may be coupled to one or more of the conductive wires or fibers in the textile substrate and may be configured to interconnect the electronic controller device 210 with the network of electrical conductive pathways. For example, the docking assembly 230 may be coupled to one or more of the conductive wires or fibers in the textile substrate via a structure that may be similar to the embodiments described herein with reference to FIG. 16.

In some embodiments, the electronic controller device 210 may include a controller device cover 212, an electronic circuit board 214, a power source 216 (e.g., rechargeable battery, or the like), and an external interface 220 (e.g., USB-C interface, or the like). The circuit board 214 may include one or more processors and memory storing processor readable instructions that, when executed, conduct operations of the electronic textile system. In some embodiments, the processor readable instructions, when executed, may conduct operations for retrieving sensory data from one or more input devices (e.g., sensors) included in the electronic textile system or for transmitting instruction signals to one or more output devices (e.g., actuators) included in the electronic textile system. To illustrate, an input device may include a temperature sensor for identifying ambient environment temperature and, in response to identifying that the ambient temperature is less than a threshold value, the processor executable instructions may conduct operations to activate one or more heating elements affixed to the textile substrate. Other embodiments of electronic controller device operations may be contemplated.

In some embodiments, the electronic controller device 210 may include a controller magnet 218. The controller magnet 218 may be a bar magnet having two polarities: north and south. Other types of magnet arrangements having two polarities may be contemplated. For example, the controller magnet 218 may be a cylindrical magnet. In some embodiments, the controller magnet 218 may be a diametrically magnetized cylindrical magnet. As will be described, the controller magnet 218 may be positioned within the electronic controller device 210 to align with a corresponding magnet in the docking assembly 230 when a portion of the electronic controller device 210 is received within the docking assembly 230. In some embodiments, the electronic controller device 210 may include a pair of controller magnets 218, where the respective controller magnets 218 may be laterally spaced magnets within the electronic controller device 210.

In some embodiments, the electronic controller device 230 may latch and unlatch from the docking assembly 230 in a direction substantially perpendicular to an interface plane of the docking assembly 230. For instance, the electronic controller device 230 may be positioned atop the docking assembly 230 for latch or unlatch operations.

As described, the docking assembly 230 may be coupled to a textile substrate having a network of electrical conductive pathways. The docking assembly 230 may include a docking cover 232, an engagement device 250, and a docking base 270.

The docking base 270 may include a cam assembly 272. In some embodiments, the cam assembly 272 may include a pair of cam components, as illustrated in FIG. 23. In the present example, the cam assembly 272 includes two cam components respectively positioned near laterally spaced portions of the docking base 270. As described herein, when the latch frame 262 is urged against portions of the cam assembly 272, the cam assembly 272 may configure the pair of latch arms 262 to spread in opposing directions (e.g., open up).

The docking base 270 includes a first electrical interface 274 for interfacing with a second electrical interface (not illustrated in FIG. 22) of the electronic controller device 230. In some embodiments, the first electrical interface 274 may include a pattern of electrical contact pads on a printed circuit board and the second electrical interface may include a pogo type connector having a 10-pin configuration layout corresponding to the pattern of electrical pads of the first electrical interface 274. Accordingly, the first electrical interface may include at least one electrical contact for interfacing with one or more pogo pins of a pogo type connector of the controller device 210.

In some embodiments, the first electrical interface 274 may be provided by a base substrate 290 positioned adjacent a textile substrate facing portion of the docking base 270. In some embodiments, the base substrate 290 may include a first substrate and a second substrate, similar to the first substrate 28 and the second substrate 30 of FIG. 1, for coupling the docking assembly 230 to the textile substrate. When the first electrical interface 274 is coupled to the second electrical interface, the electronic controller device 210 may be coupled to the network of electrical conductive pathways within the textile substrate. Other types of electrical interfaces of mating first electrical interface 274 and second electrical interface may be contemplated.

The docking assembly 230 includes an engagement device 250. The engagement device 250 may be adjustably positioned within the docking base 270. For example, the engagement device 250 may be slidable from an engage or receive position (e.g., first position) to a disengage position (e.g., second position), and vice versa. That is, movement of the engagement device 250 relative to the docking base may include slidable movement. In some embodiments, the engagement device 250 may be biased to be normally positioned in the receive position. For example, the engagement device 250 may be biased to the receive position by a spring device installed within the docking assembly. In some other embodiments, the engagement device 250 may be biased based on the structural interface between the cam assembly 272 and the one or more latch arms 262.

The engagement device 250 may include an engagement through-hole 252 or engagement aperture. In the present example, the engagement through-hole may allow pass-through of the second electrical interface of the electronic controller device 230 such that the second electrical interface can mate with the first electrical interface 274, thereby interconnecting the electronic controller device 230 with the network of electrical conductive pathways in the textile substrate.

The engagement device 250 includes a deformable latch plate. The deformable latch plate 260 may include a latch frame 264 and one or more latch arms 262 attached to the latch frame 264. In the illustrated example, the deformable latch plate includes two latch arms 262, where each respective latch arm may be positioned on an opposing lateral side of the engagement through-hole 252. The deformable latch plate 260 may be horseshoe-shaped and in communication with the cam assembly 272. As will be described, the deformable latch plate may be configured to mechanically engage a plug protrusion (not illustrated in FIG. 23) of the electronic controller device 210. In some embodiments, the latch frame 264 or the one or more latch arms 262 may be constructed of metal.

In some embodiments, the engagement device 250 may be slidable relative to the docking base 270 and within structure of the docking base 270. For example, the engagement device 250 may be biased in an engage position such that the deformable latch plate 260 may engage opposing portions of the plug protrusion of the electronic controller device 210 when the electronic controller device 210 mates with the docking assembly 230. When it is desirable to undock the electronic controller device 210 from the docking assembly 230, the engagement device 250 may be transitioned to a disengage position such that the latch frame 264 may be urged against the cam assembly to disengage the plug protrusion of the electronic controller device 210. The engagement device 250 may include a button-like interface and, upon movement of the engagement device away from the engage position, the latch frame 264 may be urged against portions of the cam assembly and configure the pair of latch arms 262 to spread in opposing directions to disengage the plug protrusion of the electronic controller device 210.

The engagement device 250 may include one or more dual purpose magnets 254. In the present example, the engagement device 250 may include a pair of magnets. In some embodiments, each of the magnets may be a cylindrical magnet. The base of the cylindrical magnet may be magnetized as a north pole, as shown in FIG. 23. Each respective magnet may be positioned on an opposing side of the engagement through-hole 252. As the engagement device 250 slides away from the engage position to the disengage position, or vice versa, the respective dual purpose magnets 254 may transition from being aligned with one of the two polarities of the controller magnet 218 to the other of the two polarities of the controller magnet 218.

To illustrate, the portion of the one or more dual purpose magnets 254 interfacing with the controller device 210 may have a north magnetic pole. When the engagement device 250 is in the engage position, the respective dual purpose magnets 254 may be aligned with the portion of the controller magnet 218 having a south magnetic pole. The alignment of opposite pole magnets may result in an attraction force contributing to retention of the electronic controller device 210 to the docking assembly 230.

When the engagement device 250 is in the disengage position, the respective dual purpose magnets 254 (e.g., having a north magnetic pole) may be aligned with the portion of the controller magnet 218 having a north magnetic pole. The alignment of oppositely polarized magnets may result in a repulsion force contributing to de-coupling of the electronic device 210 from the docking assembly 230. In the present example, alignment of the respective dual purpose magnets 254 with the portion of the controller magnet 218 having the same polarity may coincide with the deformable latch plate being urged against the cam assembly to disengage the plug protrusion of the electronic controller device 210. Accordingly, when the engagement device 250 is in the disengage position, the electronic controller device 210 may be removed from the docking assembly 230.

In some embodiments described herein, magnets may be made from rare earth materials, such as Neodynium-Iron-Boron (NdFeB), Samarium-cobalt, as are generally available. Such magnets may also be made from iron, nickel, or other suitable alloys.

In some embodiments, the engagement device 250 may be biased to be normally positioned in the engage position. When a user of the electronic textile system desires to remove the controller device 210 from the docking assembly 230, the user may push or slide the engagement device 250 away from the engage position. Accordingly, the one or more dual purpose magnets 254 may be aligned with a portion of the one or more controller magnets 218 having the same magnetic polarity, thereby providing a repulsion force as between the controller device 210 and the docking assembly 230. Substantially simultaneously, when the user pushes or slides the engagement device 250 away from the engage position, the deformable latch plate in communication with the cam assembly 272 may urge the pair of latch arms 262 to spread in opposing directions, thereby mechanically releasing the controller device 210 from the docking assembly 230.

The docking cover 232 may be configured to mate with the docking base 270 such that the engagement device 250 is received between the docking cover 232 and the docking base 270. The docking cover 232 may include a cover through-hole 234 that substantially aligns with the engagement through-hole 252 of the engagement device 250. In some embodiments, the cover through-hole 234 may be circular and may have a diameter larger than the engagement through-hole 252.

In some embodiments, the docking cover 232 may include a cover protrusion 236. The cover protrusion 236 may be positioned to align with a corresponding indentation of the electronic controller device 210 when the electronic controller device 210 is docked to the docking assembly 230. That is, the cover protrusion 236 may be positioned to assist with aligning a position of the electronic controller device 210 relative to the docking assembly 230 when the electronic controller device 210 is docked to the docking assembly 230. In the example embodiments described with reference to FIG. 23, when the electronic controller device 210 is docked and aligned to the docking assembly 230, the first electrical interface 274 (e.g., of docking assembly 230) may mate with the second electrical interface (not illustrated in FIG. 23) to provide an expected or desired electrical connection between the electronic controller device 210 and a textile substrate.

Being able to align the electronic controller device 210 to the docking assembly 230 in an expected way may be desirable in embodiments where the first electrical interface 274 may include a combination of discrete electrical contact pads, where each of the electrical contact pads may have a discrete function. In example embodiments where the first electrical interface 274 includes dense or small electrical contact pads, a specific alignment with the second electrical interface (e.g., contact pins of a pogo pin connector) on the electronic controller device 210 may be required. In scenarios where the electronic controller device 210 is misaligned with the docking assembly 230, the electrical contact pads of the first electrical interface 274 may not mate with corresponding contact pins of the second electrical interface. In such a scenario, an expected electrical connection between the electronic controller device 210 and the docking assembly 230 may not be made.

Figure 24:
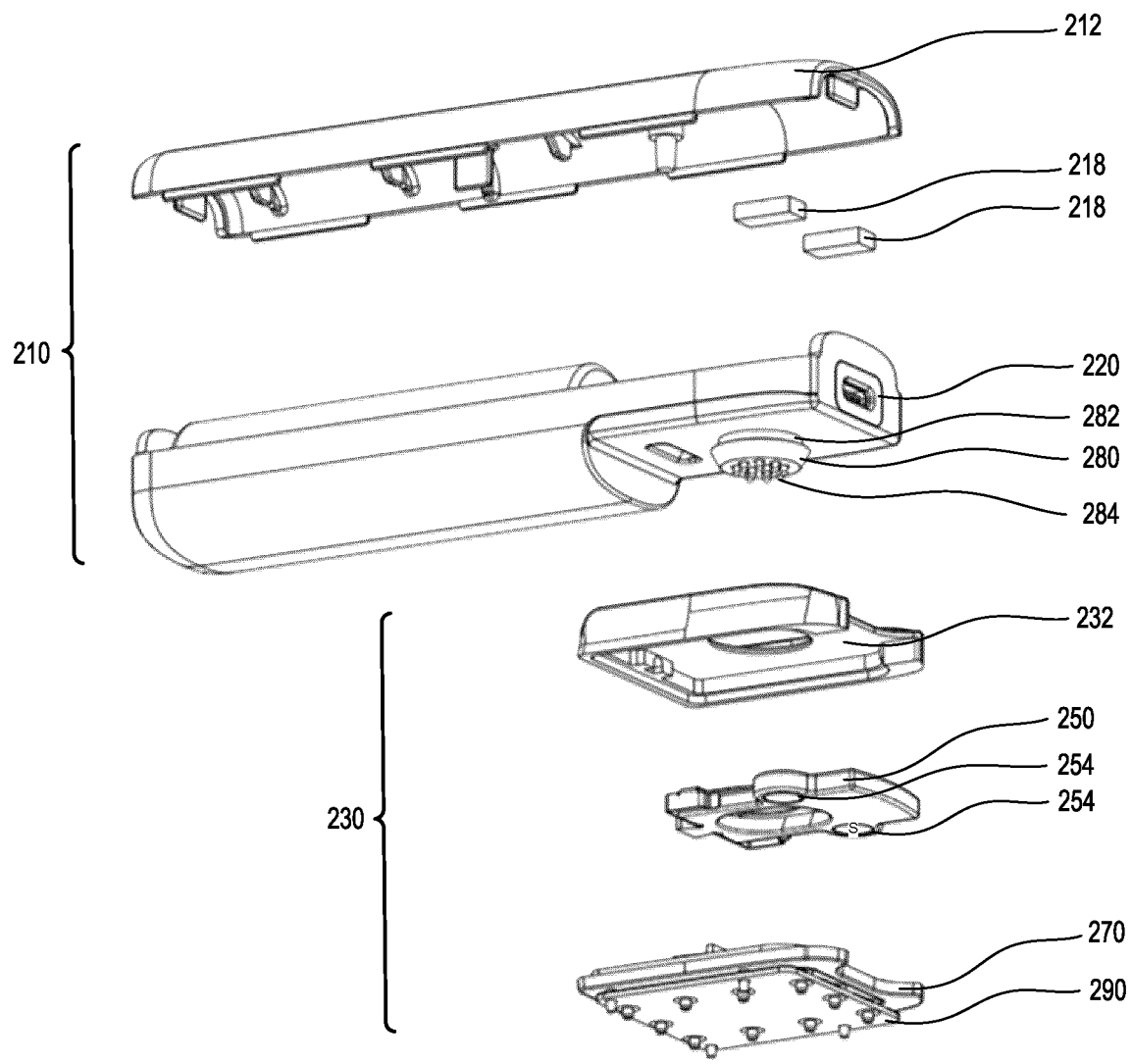
FIG. 24 illustrates an exploded bottom perspective view of the electronic controller device and the docking assembly of FIG. 23.

Reference is made to FIG. 24, which illustrates an exploded bottom perspective view of the electronic controller device 210 and the docking assembly 230 of FIG. 23. The electronic controller device 210 may include a plug protrusion 280 extending from the electronic controller device 210. For example, the plug protrusion 280 may include a cylindrical structure having a frusto-conical profile. Further, the plug protrusion 280 may include an undercut portion 282 having a cross-sectional diameter less than a cross-sectional diameter of an interfacing portion of the plug protrusion 280. The interfacing portion of the plug protrusion 280 may include the second electrical interface 284.

In some embodiments, the second electrical interface 284 may include a spring-loaded or tension-biased connector. The spring-loaded or tension-biased connector may be a connector including interface elements that may be biased or compressed in vertical and/or horizontal directions relative to a surface of the second electrical interface 284. In some examples, the spring-loaded or tension-biased connector may be a pogo-pin type connector for interfacing with electrical contact pads of the first electrical interface 274 (FIG. 23). The second electrical interface 284 of FIG. 24 includes a 10-pin pogo-pin type connector. In some examples, the spring-loaded or tension-biased connector may include a spring leaf, stamped metal (or other type of material) spring finger, or butterfly structure. The spring-loaded or tension-biased connector may have at least a portion having a spring constant and may be biased in a direction towards a corresponding contact pad of the first electrical interface 274. The spring-loaded or tension-biased connector may be based on how a metal portion is stamped or manufactured and may have a spring constant property. Other types of connectors for the second electrical interface 284 may be contemplated.

As described, when the controller device 210 may be received by the docking assembly 230, the one or more latch arms 262 may mechanically engage the plug protrusion 280 about the undercut portion 282. As described, the undercut portion 282 may be configured to have a cross-sectional diameter less than a cross-sectional diameter of an interfacing portion of the plug protrusion 280. When the engagement device 250 is in the engage position, the one or more latch arms 262 may be nestled around the undercut portion 282 of the plug protrusion 280 and may mechanically engage the plug protrusion of the controller device 210 to align the first electrical interface 274 with the second electrical interface 284.

In the exploded bottom perspective view of the engagement device 250, the portion of the dual purpose magnet 254 facing the docking base 270 may have a south magnetic polarity.

In some examples, one or a combination of the controller magnets 218 or the dual purpose magnets 254 may be arranged in combination with a Hall effect sensor for sensing when the controller device 210 and the docking assembly 230 may be in relatively close proximity for indicating that the first electrical interface 274 may be in contact with the second electrical interface 284. When the first electrical interface 274 may be in contact with the second electrical interface 284, the controller device 210 may establish an electrical connection with the docking assembly 230.

It may be appreciated that while the controller magnets 218 may be illustrated as bar magnets and that the dual purpose magnets 254 may be illustrated as cylindrical magnets, the above-described magnets may be any other shape or type and may be magnetized in any other way (e.g., radially, diametrically, etc.). Further, in some examples, when the controller magnets 218 or the dual purpose magnets 254 are provided as magnet pairs or a combination of several magnets, magnets having a smaller size and generating smaller magnetic fields may be used as a combination to achieve a similar magnetic force of attraction as a single large magnet.

Figure 25:
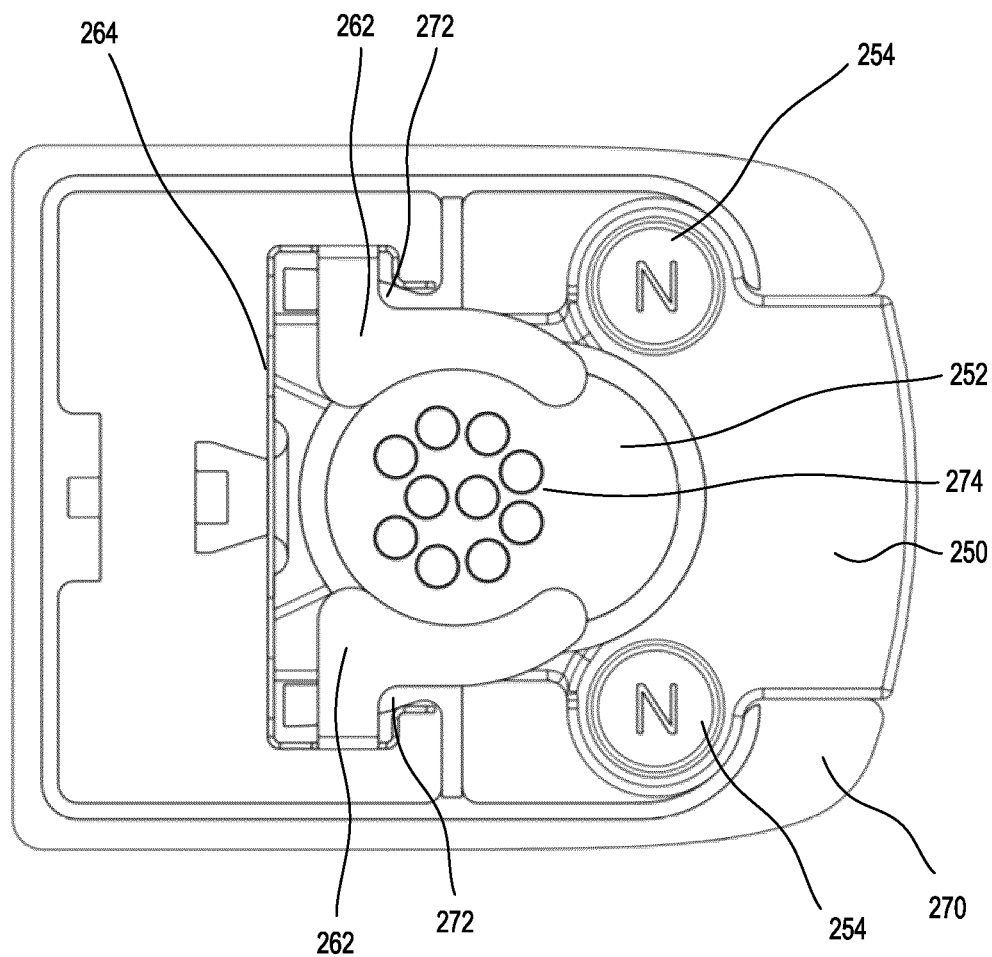
FIG. 25 illustrates a top cutaway view of the docking assembly of FIG. 23.

Reference is made to FIG. 25, which illustrates a top cutaway view of the docking assembly 230 of FIG. 23. In FIG. 25, the engagement device 250 may be biased in an engage or receive position. When the engagement device is in the engage position, the pair of latch arms 262 may be on opposing sides of the engagement through-hole 252. When the controller device 210 is received by the docking assembly 230, the pair of latch arms 262 may be positioned to surround the undercut portion 282 of the plug protrusion 280 of the controller device 210. Thus, the first electrical interface 274 including electrical contact pads may align with the second electrical interface 284 (FIG. 24) such that the controller device 210 may establish an electrical connection with an electrical conductive pathway network integrated in the textile substrate.

Figure 26:
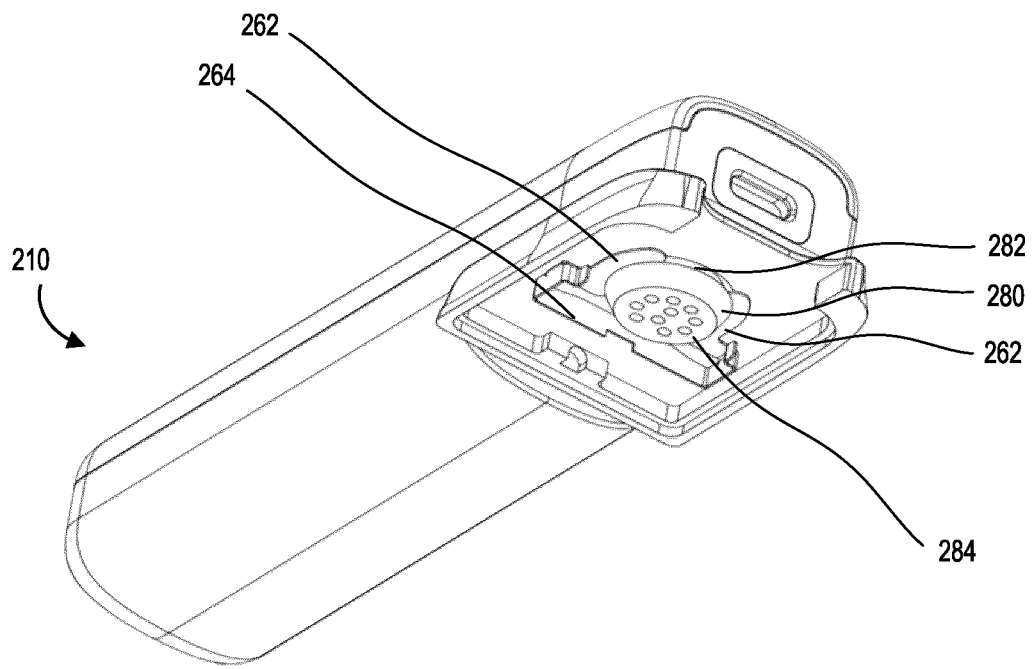
FIG. 26 illustrates a partial bottom perspective view of the electronic controller device engaged with the docking assembly of FIG. 23.

Reference is made to FIG. 26, which illustrates a partial bottom perspective view of the electronic controller device 210 engaged with the docking assembly 230 of FIG. 23. For ease of exposition, portions of the docking assembly 230 are not illustrated so as to highlight features of the engagement device 250 for mechanically engaging the plug protrusion 280 of the electronic controller device 210.

When the engagement device 250 is in the engage or receive position, the latch frame 264 may position the pair of latch arms 262 to engage opposing portions of the plug protrusion 280. In particular, the latch frame 264 may position the pair of latch arms 262 to engage opposing portions of the undercut portion 282 for mechanically engaging the controller device 210 to the docking assembly 230 to align the first electrical interface (not illustrated in FIG. 26) with the second electrical interface 284.

As the undercut portion 282 may have a cross-sectional diameter less than a cross-sectional diameter of an interfacing portion of the plug protrusion 280 nearer to the second electrical interface 284, the pair of latch arms 262 may be nestled within the undercut portion 282 to mechanically grasp the electronic controller device 210.

Figure 27:
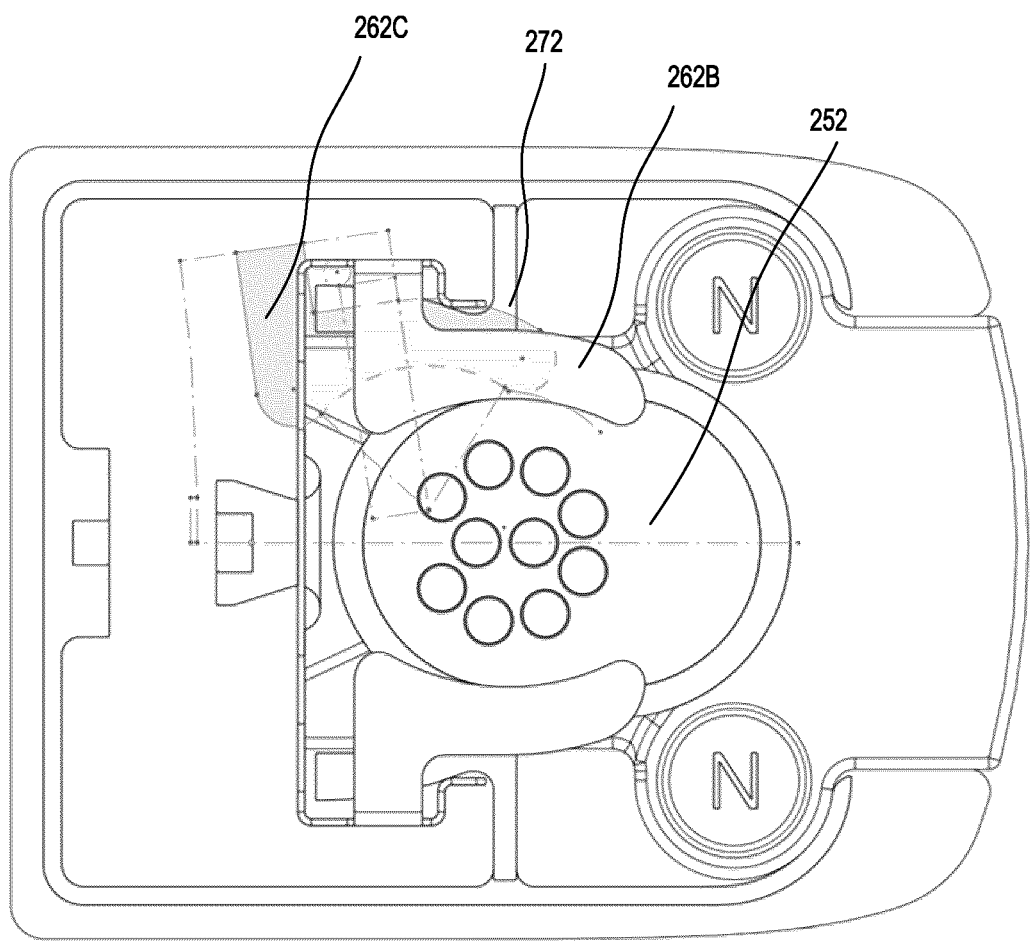
FIG. 27 illustrates a top cutaway view of the docking assembly of FIG. 23.

Reference is made to FIG. 27, which illustrates a top cutaway view of the docking assembly 230 of FIG. 23. In FIG. 27, the engagement device 250 may be in a disengage position. For instance, the user of the electronic textile system may desire to remove the electronic controller device 210 from the docking assembly 230 and may move the engagement device 250 away from the engage or receive position.

To illustrate, when the engagement device 250 is in the receive position, the pair of cam arms may be on opposing sides of the engagement through-hole 252. For ease of exposition, when the engagement device 250 is in the receive position, a cam arm is identified with reference numeral 262B.

Upon moving the engagement device 250 away from the receive position (e.g., to a disengage position), the engagement device 250 may urge the deformable latch plate (including the latch frame 264 and the pair of latch arms) against cam components of the cam assembly 272. When components of the deformable latch plate are urged against cam components of the cam assembly 272, the pair of latch arms may spread in opposing directions away from the engagement through-hole 252, thereby disengaging the pair of latch arms from the undercut portion 282 of the plug protrusion.

For ease of exposition, in FIG. 27, when the engagement device 250 is moved away from the engage position, a cam arm is identified by reference numeral 262C, illustrating the relative position of the spread cam arm to the engagement through-hole 252. When the pair of cam arms are spread in opposing directions, the docking assembly 230 releases mechanical engagement of the plug protrusion of the controller device 210. That is, the controller device 210 may be separated from the docking assembly 230.

Figure 28:
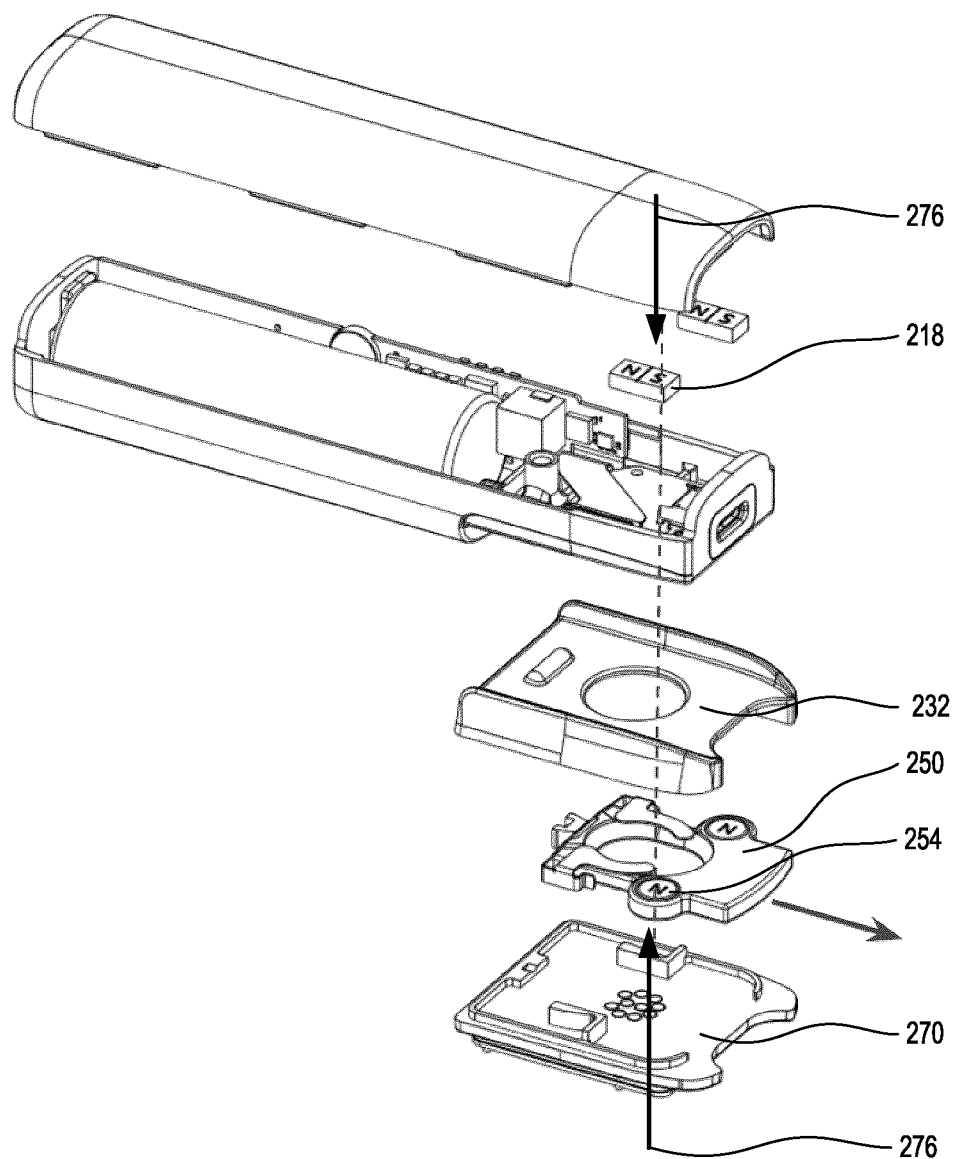
FIG. 28 illustrates an exploded perspective view of the electronic controller device and the docking assembly of FIG. 23.

Reference is made to FIG. 28, which illustrates an exploded perspective view of the electronic controller device 210 and the docking assembly 230 of FIG. 23. When the engagement device 250 is in the receive position, the one or more dual purpose magnets 254 may be aligned with an opposing magnetic pole of the corresponding controller magnet 218.

For ease of exposition, the one or more dual purpose magnets 254 may have a north magnetic pole facing the electronic controller device 210. Further, the one or more controller magnets 218 may be a bar magnet having a north magnetic pole and a south magnetic pole interfacing with the engagement device 250. Thus, when the engagement device 250 is in the receive position, the one or more dual purpose magnets 254 (e.g., north magnetic pole portion) may be in alignment with an opposing magnetic pole portion of a controller magnet 218. Alignment of opposing magnetic pole portions may cause magnetic attraction forces to mechanically couple the electronic controller device 210 to the docking assembly 230 for establishing an electrical connection (e.g., first electrical interface 274 of FIG. 23 mating with the second electrical interface 284 of FIG. 24). In FIG. 28, the magnetic attraction forces are illustrated as arrows having reference numeral 276.

As illustrated, the engagement device 250 may include two dual purpose magnets 254 positioned on opposing lateral sides of the engagement device 250. In some embodiments, the dual purpose magnets 254 may be cylindrical magnets. The electronic controller device 210 may include two controller magnets 218 positioned on opposing lateral sides of the electronic controller device 210. Accordingly, the positioning and combination of the dual purpose magnets 254 and the controller magnets 218 may rotationally align the first electrical interface 274 to the second electrical interface 284. Rotational alignment of the first electrical interface 274 with the second electrical interface 284 may be desirable when the respective electrical interfaces include two or more electrical contact points arranged in a fixed configuration. For instance, the first electrical interface 274 includes electrical contact pads in a fixed footprint arrangement.

In some example embodiments, the engagement device 250 may be movable by a user between the receive position (e.g., when the north pole facing the electronic controller device aligns with a south pole of the controller magnet 218 of the electronic controller device). In some example embodiments, the engagement device 250 may be biased to be normally positioned in the receive position, such that the docking assembly 230 may be configured for latching to a received electronic controller device 210.

Figure 29:
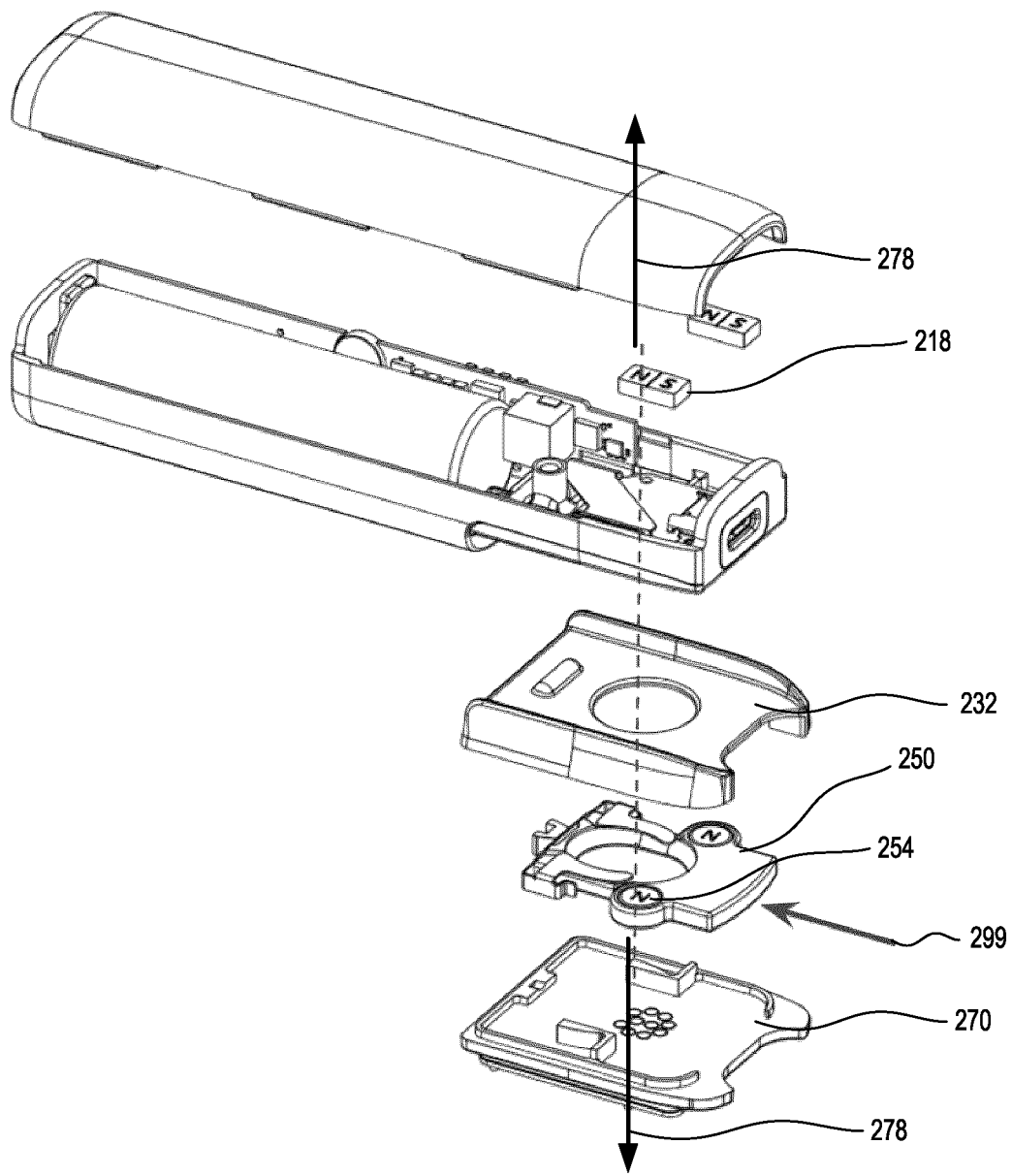
FIG. 29 illustrates an exploded perspective view of the electronic controller device and the docking assembly of FIG. 23.

Reference is made to FIG. 29, which illustrates an exploded perspective view of the electronic controller device 210 and the docking assembly of FIG. 23. In FIG. 29, the engagement device 250 may be moved or biased to a position away from the receive position. For instance, a user of the electronic textile system may push (e.g., indicated in FIG. 29 by reference numeral 299) the engagement device 250 in a direction away from the receive position towards a disengage position.

When the engagement device 250 is biased to a position away from the receive position, the one or more dual purpose magnets 254 may transition to being aligned with a similar magnetic pole of the corresponding controller magnet 218.

As in FIG. 28, the one or more dual purpose magnets 254 may have a north magnetic pole facing the electronic controller device 210. Further, the one or more controller magnets 218 may be a bar magnet having a north magnetic pole and a south magnetic pole interfacing with the engagement device 250. When the engagement device 250 is in the disengage position, the one or more dual purpose magnets 254 (e.g., north magnetic pole portion) may be in alignment with the north magnetic pole portion of a corresponding controller magnet 218. Alignment of similar magnetic pole portions may cause magnetic repulsion forces to mechanically repel the electronic controller device 210 from the docking assembly 230. In FIG. 29, the magnetic repulsion forces are illustrated as arrows having reference numeral 278.

Based at least on the foregoing description of the electronic controller device 210 and the docking assembly 230 of FIG. 23, the engagement device 250 may include an arrangement of magnets to provide magnetic attraction forces to mechanically couple the electronic controller device 210 to the docking assembly 230. Further, the arrangement of magnets may assist with rotationally aligning the first electrical interface 274 (of the docking assembly 230) and the second electrical interface 284 (of the electronic controller device 210).

Further, the foregoing description of the docking assembly 230 of FIG. 23 includes a deformable latch plate having an arrangement of one or more latch arms that may mechanically engage or disengage an undercut portion 282 of the plug protrusion 282 of the electronic controller device 210.

According, as described, when the engagement device 250 is biased to move away from the receive position: (1) the arrangement of magnets may cause repulsion forces to separate the electronic controller device 210 from the docking assembly 230; and, substantially simultaneously; or (2) the arrangement of a deformable latch plate of the engagement device 250 may disengage an undercut portion 282 of the electronic controller device 210 allowing the electronic controller device 210 to be mechanically separated from the docking assembly 230.

Figure 30:
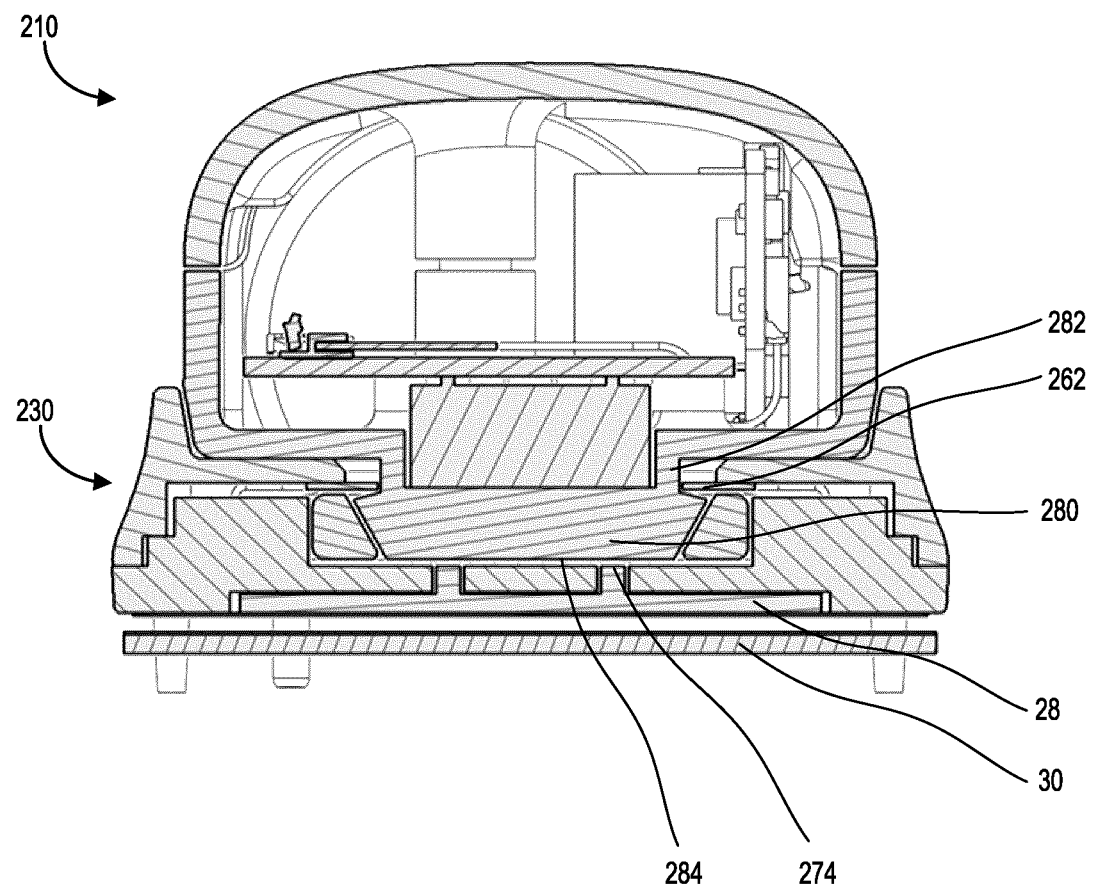
FIG. 30 illustrates a cross-sectional view of an electronic controller device received by a docking assembly, in accordance with an example embodiment of the present application.

Reference is made to FIG. 30, which illustrates a cross-sectional view of the electronic controller device 210 received by the docking assembly 230, in accordance with an example of the present application.

In FIG. 30, the pair of latch arms 262 may be positioned on opposing sides of the engagement through-hole 252 (FIG. 23) and may be engaging the undercut portion 282 of the plug protrusion 280. As the cross-sectional diameter of the undercut portion 282 may be less than a cross-sectional diameter of an interfacing portion of the plug protrusion 280, the pair of latch arms 262 may mechanically engage the plug protrusion about the undercut portion 282 when the engagement device 250 is in the receive position within the docking base 270.

In FIG. 30, the docking assembly 230 may be attached to the textile substrate based on a configuration described with reference to FIG. 1. For example, the docking assembly 230 may include a first substrate 28 (similar to the first substrate 28 of FIG. 1) coupled adjacent the first electrical interface 274. Further, the docking assembly 230 may include a second substrate 30 (similar to the second substrate 30 of FIG. 1). The textile substrate (not illustrated in FIG. 30) may be received between the first substrate 28 and the second substrate 30. Accordingly, the docking assembly 230 may be electrically coupled to an electrical conductive pathway network integrated in the textile substrate. When the electronic controller device 210 is received by the docking assembly 230, the electronic controller 210 may be electrically coupled to the electronic conductive pathway network for transmitting or receiving signals to or from devices of the electrical conductive pathway network.

Figure 31:
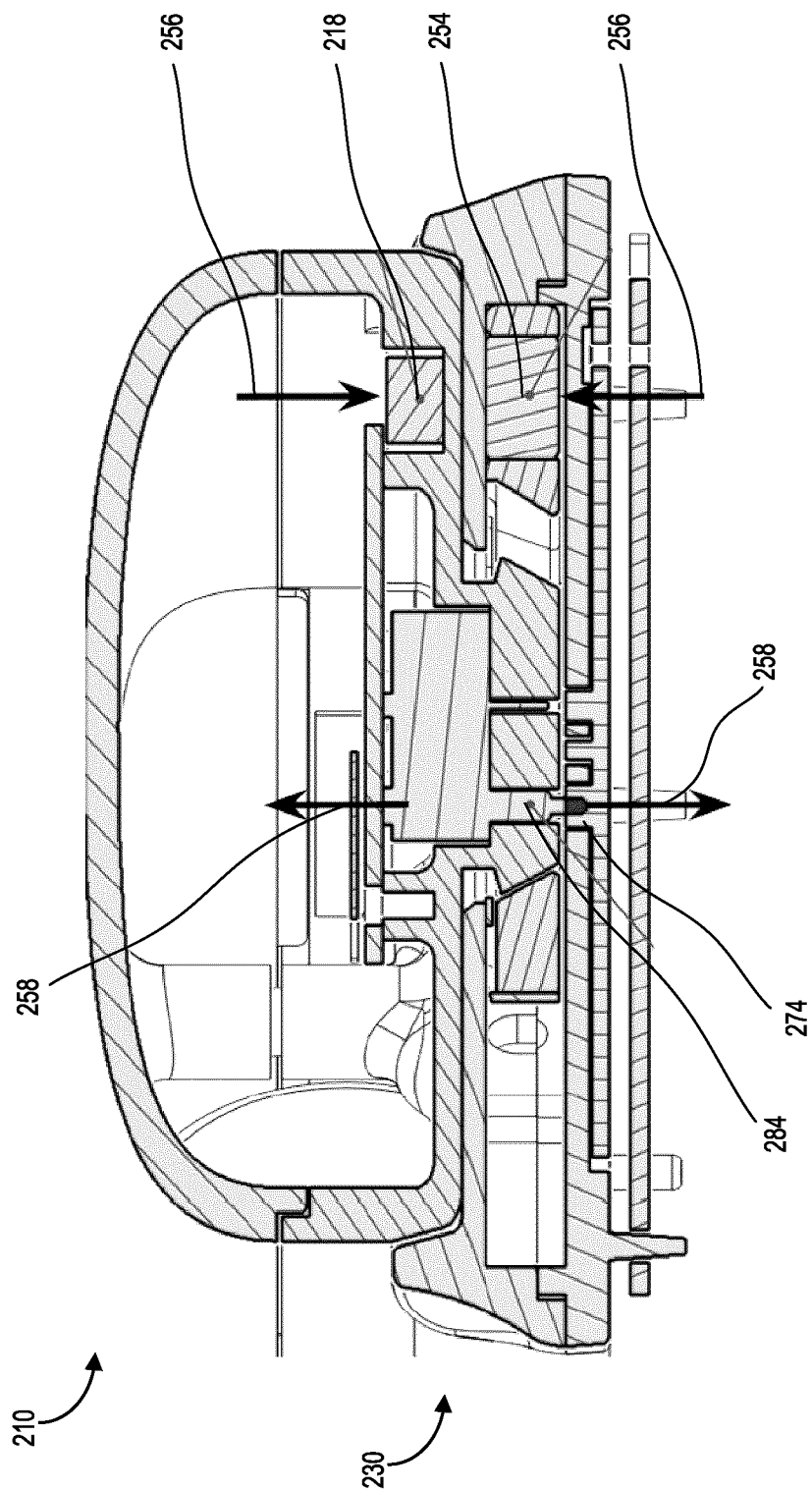
FIG. 31 illustrates a cross-sectional view of an electronic controller device received by a docking assembly, in accordance with another example embodiment of the present application.

Reference is made to FIG. 31, which illustrates another cross-sectional view of the electronic controller device 210 received by the docking assembly 230, in accordance with another example embodiment of the present application.

In FIG. 31, the electronic controller device 210 includes the controller magnet 218 and the docking assembly 230 includes the dual purpose magnets 254. A single controller magnet 218 and a single dual purpose magnet 254 is illustrated in FIG. 31; however, it may be appreciated that the electronic controller device 210 and the docking assembly 230 may have magnet pairs.

In the scenario when the dual purpose magnet 254 (e.g., north magnetic pole) is aligned with a portion of the controller magnet 218 having an opposing magnetic pole (e.g., south magnetic pole), an attraction force illustrated with arrows identified with reference numeral 256 between the electronic controller device 210 and the docking assembly 230 will be experienced.

In the electronic controller device 210, the second electrical interface 284 may include a pogo pin connector. A pin of the pogo pin connector may exert a spring biasing force causing a separation force (illustrated by arrows identified with reference numeral 258) between the first electrical interface 274 and the second electrical interface 284. Accordingly, substantially simultaneously, the attraction force (illustrated with reference numeral 256) based on alignment of the controller magnet 218 and the dual purpose magnet 254 may counteract the biasing force (illustrated with reference numeral 258) caused by the spring biasing force of the second electrical interface 284.

Figure 32:
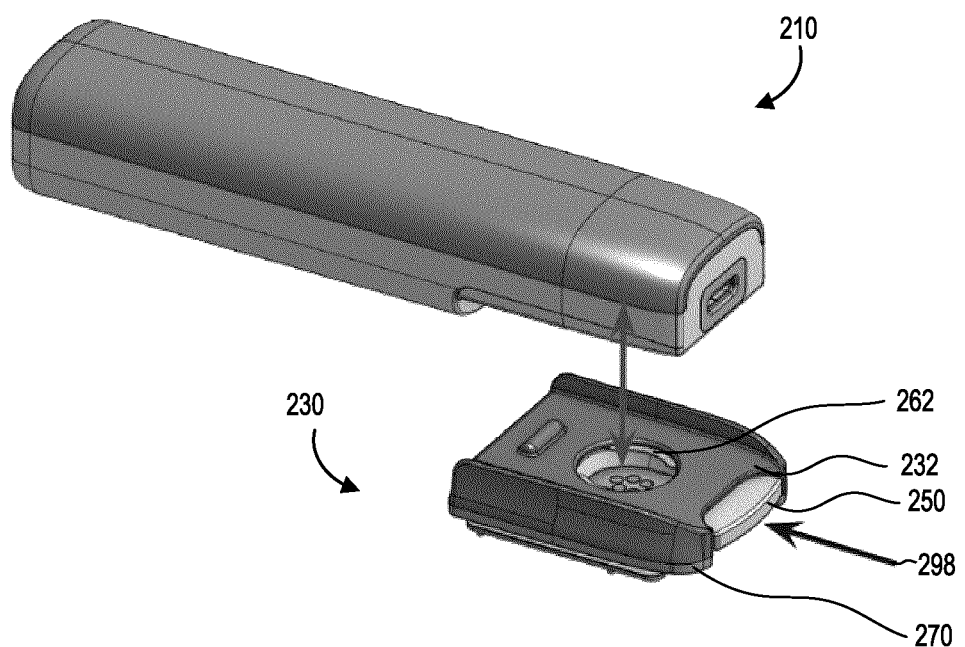
FIG. 32 illustrates a perspective view of the electronic controller device and the docking assembly of FIG. 23 in assembled form, in accordance with an example embodiment of the present application.

Reference is made to FIG. 32, which illustrates a perspective view of the electronic controller device 210 and the docking assembly 230 of FIG. 23 in assembled form, in accordance with an example of the present application.

In FIG. 32, the engagement device 250 is assembled between the docking cover 232 and the docking base 270. A user of the electronic textile system may impart slidable movement of the engagement device 250 relative to the docking base 270 by pressing the engagement device 250 in a direction indicated by an arrow identified by reference numeral 298. Accordingly, when the engagement device 250 is moved away from the receive position (e.g., in the direction of the arrow identified by reference numeral 298), the electronic controller device 210 may be unlatched and separated from the docking assembly 230.

In some scenarios, the electronic controller device 210 may be latched to the docking assembly 230 based at least on: (1) one or more latch arms 262 mechanically engaging a plug protrusion (not illustrated) of the electronic controller device 210; or (2) magnetic attraction forces based on alignment of opposite magnetic pole portions of the one or more dual purpose magnets (not illustrated) of the docking assembly 230 and the one or more controller magnets (not illustrated) of the electronic controller device 210.

Based on example embodiments described herein, when the engagement device 250 is slid in the direction of the arrow identified by reference numeral 298, the one or more dual purpose magnets (not illustrated in FIG. 32) of the engagement device 250 may be aligned with a similar magnetic pole portion of a corresponding one or more controller magnets (not illustrated in FIG. 32) of the electronic controller device 210. When the engagement device 250 is slid in a direction away from the receive position, the arrangement of magnets may cause a repulsion magnetic force, thereby separating the electronic controller device 210 from the docking assembly 230.

In FIG. 32, the electronic controller device 210 may latch or unlatch from the docking assembly 230 in a direction that may be substantially perpendicular to the direction that the engagement device 250 moves within the docking base 270.

Figure 33:
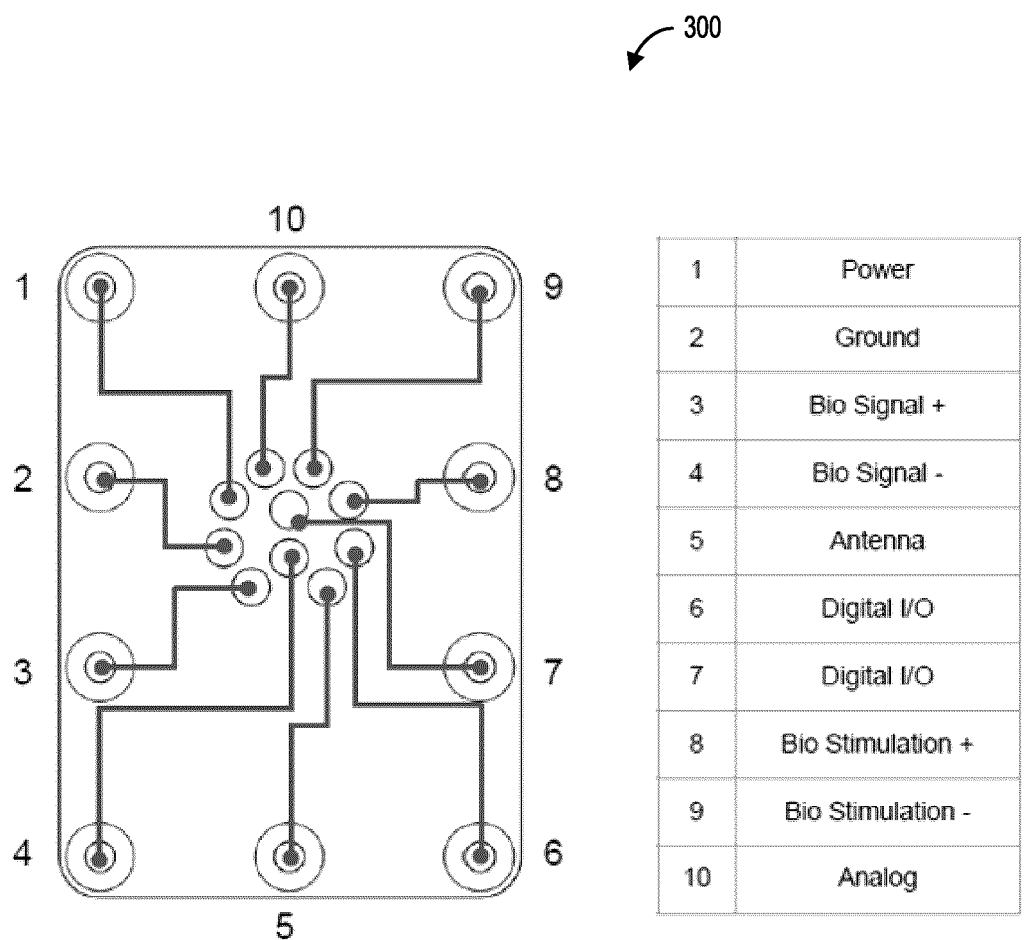
FIG. 33 illustrates a pinout diagram of the first electrical interface and corresponding conductive traces to printed circuit board vertical interconnect access points, in accordance with an example embodiment of the present application.

Reference is made to FIG. 33, which illustrates a pinout diagram 300 of the first electrical interface 284 and corresponding conductive traces to printed circuit board (PCB) vertical interconnect access (VIA) points, in accordance with an example of the present application. For instance, the PCB may be the first substrate 28 (FIG. 30) positioned adjacent the docking base 270.

The first electrical interface 274 may include a combination of electrical contact pads for mating with a 10-pin pogo connecter of the second electrical interface 284. For instance, the 10-pin pogo connector may include signals such as power, ground, bio (+ve), bio (−ve), antenna, digital I/O, bio simulation (+ve), vio simulation (−ve), or analog signals. In some embodiments, the one or more signals may be routed to one or more input sensors coupled to the electrical conductive pathway network integrated in a textile substrate. In some embodiments, the one or more signals may be routed to one or more actuators coupled to the electrical conductive pathway network integrated in a textile substrate.

It may be appreciated that although the first electrical interface 274 may be an arrangement of electrical contact pads for interfacing with a 10-pin pogo connector, any other arrangement of one or more electrical contact pads may be contemplated for interfacing with any other type of electrical connector of the electronic controller device 210.

Figure 34:
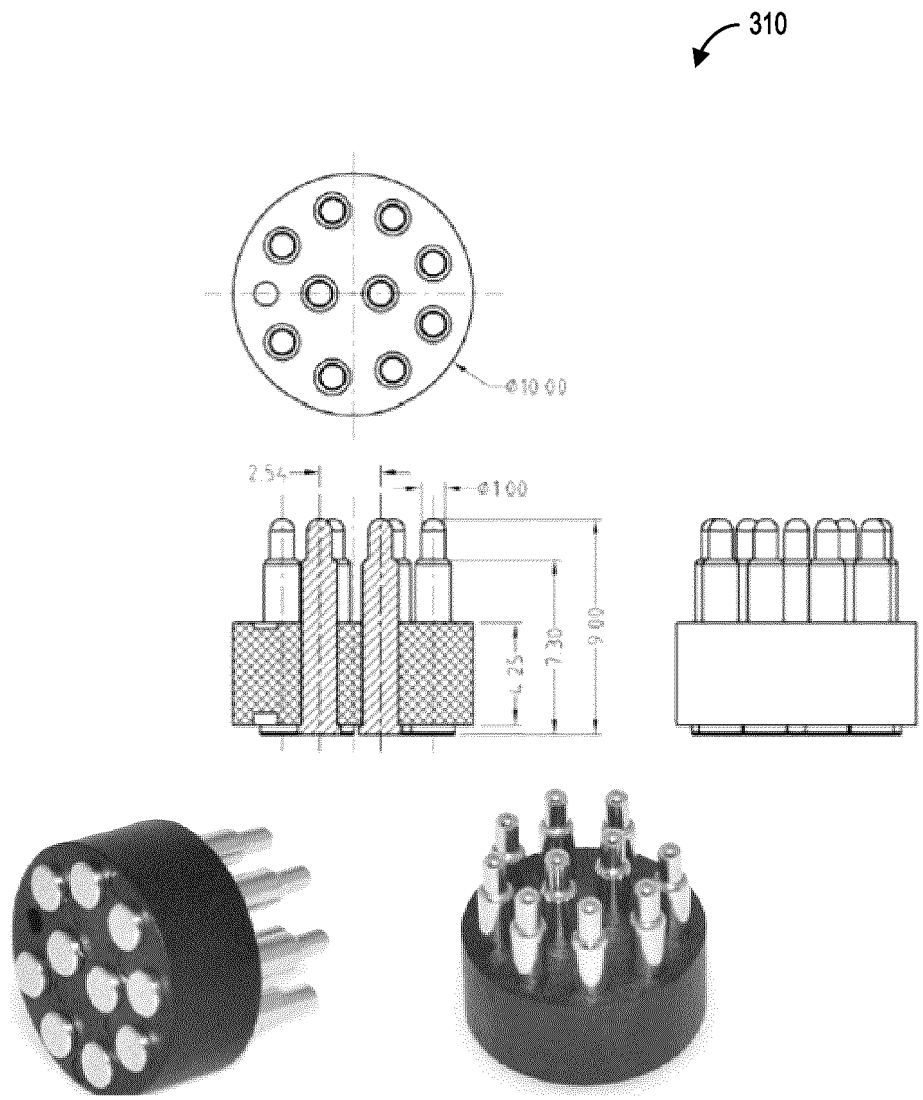
FIG. 34 illustrates a partial mechanical connector data sheet of an example 10-pin pogo connector, in accordance with an example embodiment of the present application.

Reference is made to FIG. 34, which illustrates data sheet drawings 310 of an example 10-pin pogo connector associated with the second electrical interface 284. In some embodiments, the second electrical interface 284 may include the 10-pin pogo connector for establishing an electrical connection with contact pads of the first electrical interface 274 (e.g., when the electronic controller device 210 is received by the docking assembly 230.

Figure 35B:
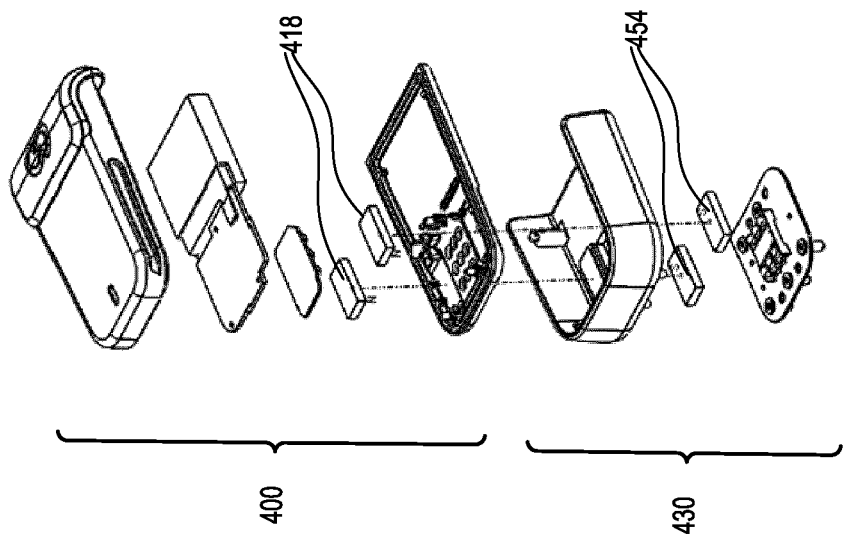
FIGS. 35A and 35B illustrate exploded perspective views of a variant controller device and a variant docking assembly, in accordance with an example embodiment of the present application.
Figure 35A:
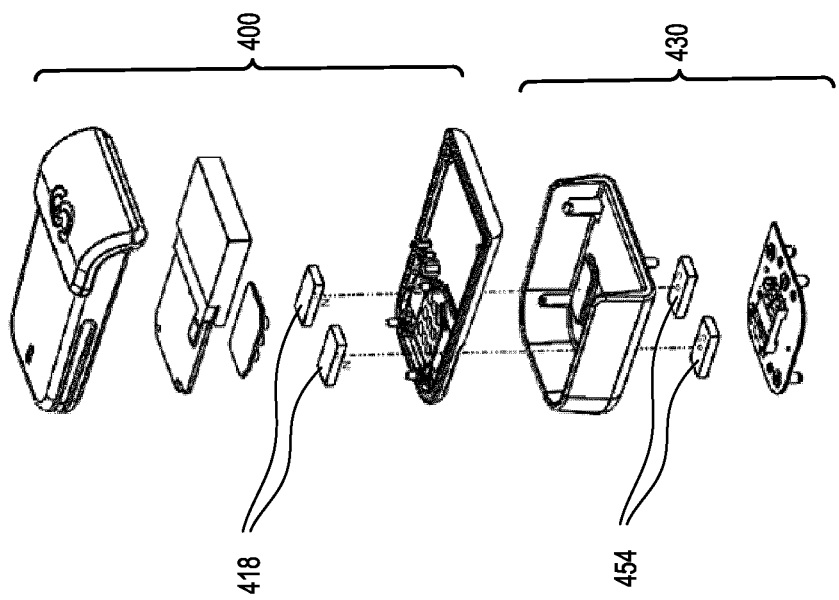

Reference is made to FIGS. 35A and 35B, which illustrate exploded perspective views of a variant controller device 400 and a variant docking assembly 430, in accordance with an example of the present application. The variant controller device 400 may include features similar to features of the controller device 12 of FIG. 1 and the variant docking assembly 430 may include features similar to features of the docking station 14 of FIG. 1.

The variant controller device 400 may include a pair of variant controller magnets 418. The variant controller magnets may be bar magnets having a north magnetic pole facing the variant docking assembly 430. Although the variant controller magnets 418 are illustrated as bar magnets, they may be any other type of magnets. For example, the variant controller magnets 418 may be cylindrical magnets radially magnetized such that the north magnetic pole may face the variant docking assembly 430. Further, although a pair of variant controller magnets 418 is illustrated, the variant controller magnet may be a single magnet or may include any number of magnets arranged as a combination.

The variant docking assembly 430 may include a pair of dock magnets 454. The pair of dock magnets 454 may be magnets having a south magnetic pole facing the variant controller device 400 and may be positioned within the docking assembly 430 such that when the controller device 400 is received within the variant docking assembly 430, an attraction force may retain the controller device 400 within the docking assembly 430.

In some examples, not illustrated, the dock magnets 454 may include a combination of two or more magnets arranged in a particular keyed configuration. Accordingly, the docking assembly 430 may be configured such that only controller devices having magnets arranged in that corresponding keyed configuration with opposite polarity may be received and retained within the docking assembly 430. In some examples, it may be desirable to install only pre-selected controller devices with docking assemblies. Dock magnets 454 arranged in a particular keyed configuration may be used to differentiate some controller devices receivable with a given dock assembly from other controller devices not intended to be received with the given dock assembly.

For ease of exposition, if the dock magnets 454 have a south magnetic polarity facing a controller device, only controller devices having a north magnetic polarity facing the docking assembly 430 may be received within the docking assembly 430. In some other examples, the configuration and arrangement of the magnets may be any other combination. For instance, the pair of dock magnets 454 may include one south magnetic polarity and one north magnetic polarity facing the controller device 400. Any other configurations of the controller magnets and the dual purpose magnets for selectively allowing controller devices to dock with the docking assembly may be contemplated. For example, the dock magnets 454 and the complementary controller magnets 418 may be multi-pole magnet arrangements.

Figure 36B:
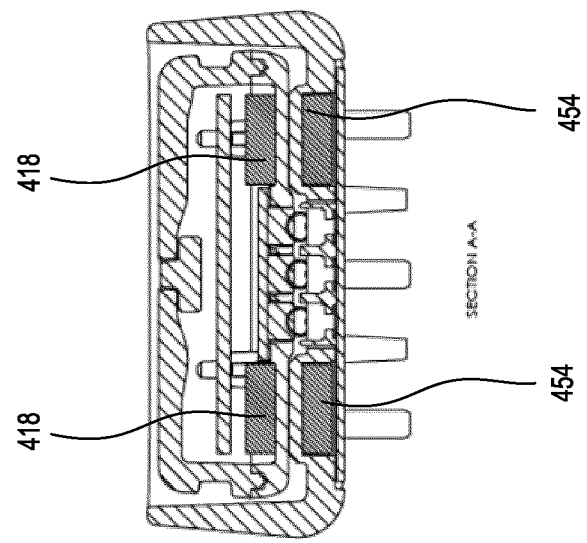
FIGS. 36A and 36B illustrate a side elevation view and a cross-sectional elevation view, respectively, of the variant controller device and the variant docking device of FIG. 35A.
Figure 36A:
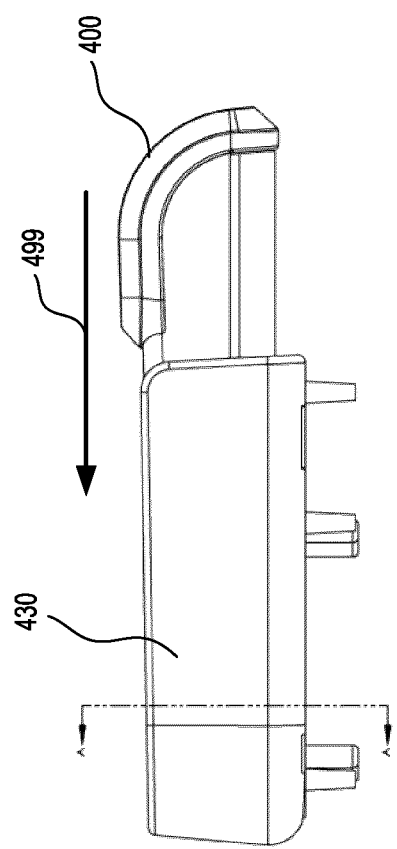

Reference is made to FIGS. 36A and 36B, which illustrate a side elevation view and a cross-sectional elevation view, respectively, of the variant controller device 400 and the variant docking device 430 of FIG. 35A.

In FIG. 36A, the variant controller device 400 is partially inserted into the variant docking device 430. The variant controller device 400 may be inserted into the variant docking device 430 in a direction indicated by the arrow identified with reference numeral 499.

In FIG. 36B, the cross-sectional view of the variant controller device 400 and the variant docking device 430 taken along line A-A is illustrated. When the variant controller device 400 is fully inserted into the variant controller device 400, the controller magnets 418 having a north magnetic polarity facing the variant docking assembly 430 may align with the dock magnets 454 having a south magnetic polarity facing the variant controller device 400. When the respective controller magnets 418 align with a corresponding respective dock magnets 454, a retention magnetic force may retain the variant controller device 400 within the variant docking assembly 430.

Figure 37:
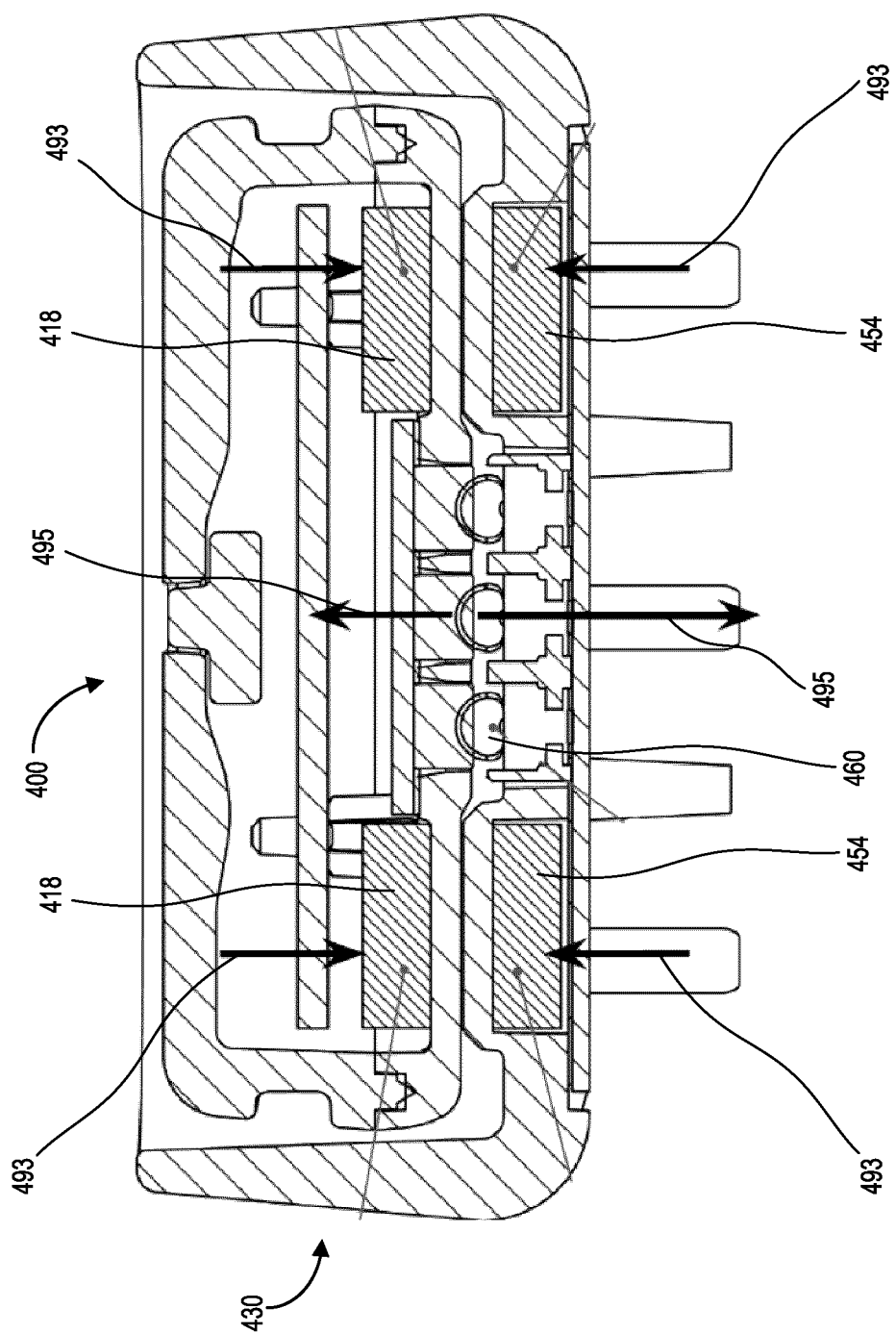
FIG. 37 illustrates the cross-sectional view of the variant controller device and the variant docking device of FIG. 36.

Reference is made to FIG. 37, which illustrates the cross-sectional view of the variant controller device 400 and the variant docking device 430 as illustrated in FIG. 36B.

The variant controller device 400 includes the controller magnets 418. In some examples, the variant docking device 430 may include an electrical dock connector 460. The electrical dock connector 460 may include spring-loaded contact pins for mating with contact pads of the variant controller device 400. The spring-loaded contact pins may exert a spring biasing force causing a separation force (illustrated by arrows identified with reference numeral 495) between the variant controller device 400 and the variant docking device 430. Accordingly, substantially simultaneously, the attraction force (illustrated with arrows identified with reference numeral 493) based on the alignment of the controller magnets 418 and the dock magnets 454 may counteract the spring biasing force caused by the spring-loaded contact pins.

In some examples, one or a combination of the controller magnets 418 or the dock magnets 454 may be arranged in combination with a Hall effect sensor (not illustrated) for sensing when the variant controller device 400 and the variant docking device 430 may be in relatively close proximity. When the variant controller device 400 and the variant docking device 430 is in substantially close proximity, a signal from the Hall effect sensor may be identified to indicate that an electrical connection may be established between the controller device 400 and the variant docking device 430.

Figure 38:
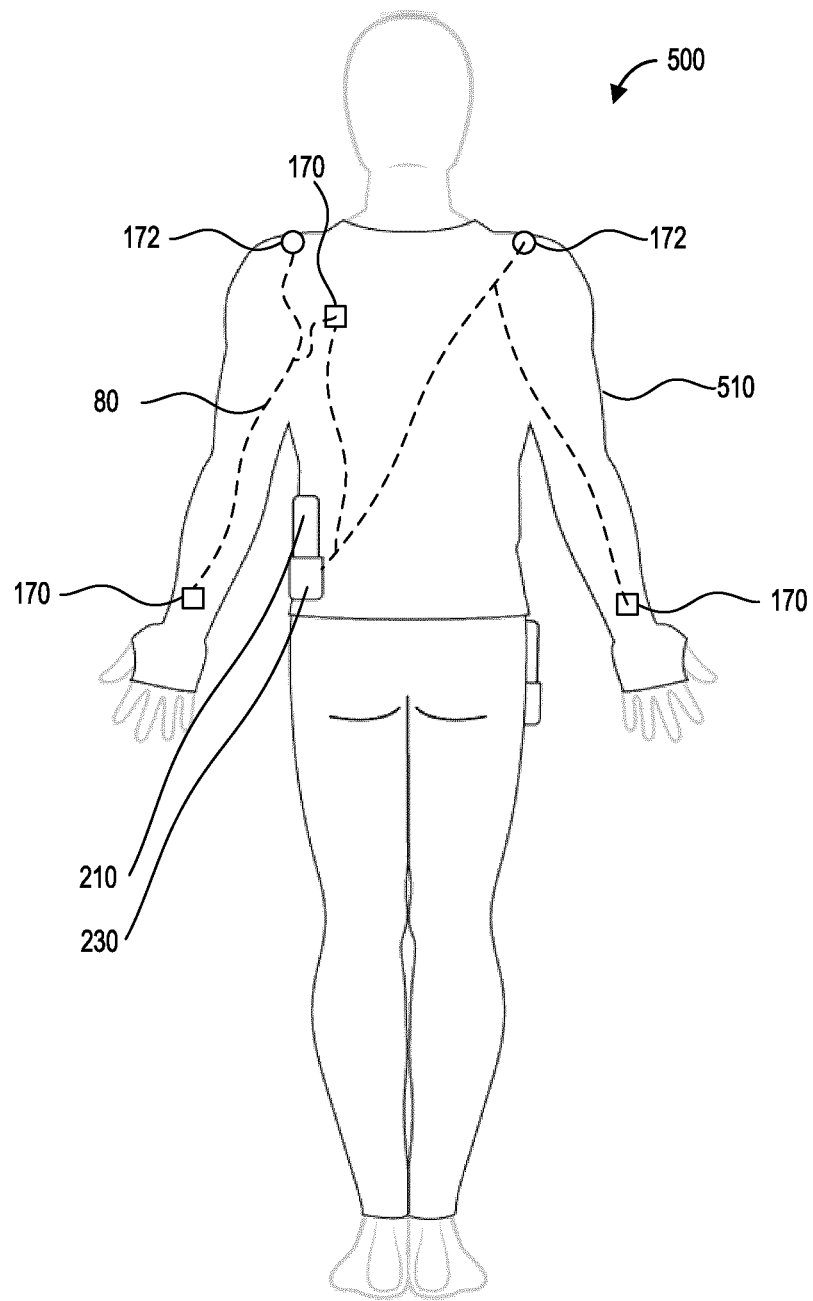
FIG. 38 illustrates a schematic diagram of an electronic textile system, in accordance with an example embodiment of the present application.

Reference is made to FIG. 38, which illustrates a schematic diagram of an electronic textile system 500, in accordance with an example of the present application. The electronic textile system 500 may include one or more input devices 170. The one or more input devices may include a temperature sensor, a moisture sensor, a respiratory monitoring sensor, a heart rate sensor, an accelerometer, a gyroscope, an electroencephalogram (EEG) sensor, electromyography (EMG) sensor, an electrocardiography (ECG) sensor, a photoplethysmography (PPG) sensor, a ballistocardiograph (BCG) sensor, a galvanic skin response (GSR) sensor, a bio-impedance sensor (or bio-electrical impedance sensor), or chemical sensors (e.g., chemical sensors for sweat, glucose, urine, or the like).

The one or more input devices 170 may be attached to the textile substrate. For instance, the one or more input devices 170 may be coupled to an electrical conductive pathway network 80 of conductive fibers interwoven, knit, or otherwise integrated in the textile substrate 510. The textile substrate 510 may be one or more shirts, pants, socks, or the like. In some embodiments, the electrical conductive pathway network may supply electrical power to the one or more input devices 170 or the one or more output devices 180.

In FIG. 38, the textile substrate 510 may be an athletic shirt. A user of the electronic textile system 500 may wear the athletic shirt during a training session. During the training session, the input devices 170 or sensors may generate signals for transmission, via the electrical conductive pathway network 80, to the electronic controller device 210. When the electronic controller device 210 is received by the docking assembly 230, the electronic controller device 210 may receive data signals from the input devices 170 and may transmit data signals or electrical power to the one or more input device 170. It may be appreciated that the electronic controller device 210 may be a data acquisition or processing computing device for tracking fitness related or physiological data during the training session.

In some embodiments, the electronic textile system 500 may include one or more output devices 172. The one or more output devices 172 may be attached to the textile substrate 510 and electrically coupled to the electrical conductive pathway network 80. In some embodiments, the one or more output devices 172 may include heating elements. For instance, in response to determining that an ambient temperature via data from an input device 170 is below a threshold temperature, the electronic controller device 170 may transmit a signal activating a heating element for providing heat to the user of the electronic textile system. Other example output devices 172 may be contemplated. For example, the one or more output devices 172 may include haptic feedback devices or visual display elements.

It may be appreciated that the electrical conductive pathway network and the configuration/arrangement of the input devices 170 or the output devices 172 are illustrative examples only. Other arrangements or configurations for coupling the docking assembly 230, the input devices 170, or the output devices 172 may be contemplated.

It may be appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The invention claimed is:

1. A docking assembly for an electronic textile system, the docking assembly comprising: a docking base including a first electrical interface for mating with a second electrical interface of a controller device receivable by the docking assembly; and an engagement device adjustably positioned within the docking base in a receive position, the engagement device including a first magnet for interacting with a second magnet of the controller device to align the first electrical interface with the second electrical interface for establishing an electrical connection, and wherein the first magnet repels the second magnet for separating the first electrical interface from the second electrical interface upon movement of the engagement device away from the receive position within the docking base, and wherein the engagement device includes a deformable latch plate mechanically engaging a plug protrusion of the controller device receivable by the docking assembly to align the first electrical interface with the second electrical interface.

2. The docking assembly of claim 1, wherein the engagement device is biased to be normally positioned in the receive position.

3. The docking assembly of claim 1, wherein movement of the engagement device relative to the docking base includes slidable movement.

4. The docking assembly of claim 1, wherein the first magnet attracts an opposing pole of the second magnet when aligning the first electrical interface and the second electrical interface.

5. The docking assembly of claim 1, wherein the first magnet includes a first pair of magnets respectively positioned on opposing lateral sides of the engagement device, and wherein the second magnet includes a second pair of magnets respectively positioned on opposing lateral sides of the controller device to correspond to respective positions of the first pair of magnets to rotationally align the first electrical interface with the second electrical interface.

6. The docking assembly of claim 1, wherein the docking base includes a cam assembly, and wherein the engagement device includes the deformable latch plate in communication with the cam assembly.

7. The docking assembly of claim 6, wherein the engagement device urges the deformable latch plate against the cam assembly to disengage the plug protrusion upon movement of the engagement device away from the receive position within the docking base.

8. The docking assembly of claim 6, wherein the deformable latch plate includes a pair of latch arms to engage opposing portions of the plug protrusion.

9. The docking assembly of claim 8, wherein the engagement device urges the pair of latch arms to spread in opposing directions when the engagement device urges the deformable latch plate against the cam assembly.

10. The docking assembly of claim 1, wherein the first electrical interface includes at least one electrical contact for interfacing with a spring-loaded connector of the controller device receivable by the docking assembly.

11. The docking assembly of claim 10, wherein the spring-loaded connector includes at least one of a pogo-pin, a spring leaf structure, a stamped metal spring finger, and a butterfly mechanism.

12. The docking assembly of claim 1, wherein the first magnet of the engagement device attracts and repels the second magnet of the controller device in a direction substantially perpendicular to a plane of the engagement device.

13. An electronic textile system comprising: a textile substrate; an input device attached to the textile substrate; a docking assembly attached to the textile substrate for removably receiving a controller device, the docking assembly including a first electrical interface for mating with a second electrical interface of the controller device; and an electrical conductive pathway network integrated in the textile substrate for electrically coupling the input device and the first electrical interface, wherein the input device transmits to the controller device electronic signals representing input data when the controller device is received by the docking assembly, and wherein the docking assembly includes: a docking base including the first electrical interface for mating with the second electrical interface of the controller device receivable by the docking assembly; an engagement device adjustably positioned within the docking base in a receive position, the engagement device including a first magnet for interacting with a second magnet of the controller device to align the first electrical interface with the second electrical interface for establishing an electrical connection, and wherein the first magnet repels the second magnet for separating the first electrical interface from the second electrical interface upon movement of the engagement device away from the receive position within the docking base, and wherein the engagement device includes a deformable latch plate mechanically engaging a plug protrusion of the controller device receivable by the docking assembly to align the first electrical interface with the second electrical interface.

14. The electronic textile system of claim 13, wherein the electrical conductive pathway network includes a network of electrical conductive fibers interwoven or knit into the textile substrate.

15. The electronic textile system of claim 13, wherein the input device includes at least one of a temperature sensor, a moisture sensor, a heart rate sensor, an accelerometer, a gyroscope, an electroencephalogram sensor, electromyography sensor, an electrocardiography sensor, a photoplethysmography sensor, a ballistocardiograph sensor, a galvanic skin response sensor, a bio-impedance sensor, or chemical sensors.

16. The electronic textile system of claim 13, including an output device coupled to the electrical conductive pathway network, the output device including at least one of a heating element, a haptic feedback element, a stimulation element, or a visual display.

17. The electronic textile system of claim 13, wherein the electrical conductive pathway network supplies electrical power to the input device when the controller device is received by the docking assembly.

18. The electronic textile system of claim 13, wherein the textile substrate is at least one of an undergarment, a shirt, a pant, a shoe, a hat, a sock, a glove, a headband, a belt, a brassiere, a balaclava, a base layer, a jacket, or a sweatshirt.

* * * * *